United States Patent
Holsing et al.

(10) Patent No.: US 7,085,400 B1
(45) Date of Patent: Aug. 1, 2006

(54) SYSTEM AND METHOD FOR IMAGE BASED SENSOR CALIBRATION

(75) Inventors: Troy Holsing, Westminster, CO (US); Gordon Goodchild, Broomfield, CO (US)

(73) Assignee: Surgical Navigation Technologies, Inc., Louisville, CO (US)

( * ) Notice: Subject to any disclaimer, the term of this patent is extended or adjusted under 35 U.S.C. 154(b) by 1010 days.

(21) Appl. No.: 09/593,495

(22) Filed: Jun. 14, 2000

(51) Int. Cl.
*G06K 9/00* (2006.01)

(52) U.S. Cl. .................. 382/103; 382/151; 382/152; 382/291

(58) Field of Classification Search ............... 382/103, 382/145, 148, 151, 154, 289, 291, 319, 152
See application file for complete search history.

(56) References Cited

U.S. PATENT DOCUMENTS

| | | |
|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,294,083 A | 12/1966 | Alderson |
| 3,367,326 A | 2/1968 | Frazier |
| 3,439,256 A | 4/1969 | Kähne et al. |
| 3,577,160 A | 5/1971 | White |
| 3,674,014 A | 7/1972 | Tillander |
| 3,702,935 A | 11/1972 | Carey et al. |
| 3,704,707 A | 12/1972 | Halloran |
| 3,868,565 A | 2/1975 | Kuipers .................. 324/34 R |
| 3,941,127 A | 3/1976 | Froning |
| 4,037,592 A | 7/1977 | Kronner |
| 4,052,620 A | 10/1977 | Brunnett |
| 4,054,881 A | 10/1977 | Raab .................. 343/112 R |
| 4,117,337 A | 9/1978 | Staats |
| 4,173,228 A | 11/1979 | Van Steenwyk et al. |
| 4,202,349 A | 5/1980 | Jones |
| 4,262,306 A | 4/1981 | Renner |
| 4,287,809 A | 9/1981 | Egli et al. |
| 4,314,251 A | 2/1982 | Raab .................. 343/112 R |
| 4,317,078 A | 2/1982 | Weed et al. |

(Continued)

FOREIGN PATENT DOCUMENTS

CA        964149        3/1975

(Continued)

OTHER PUBLICATIONS

Adams, L., et al., *Computer-Assisted Surgery*, IEEE Computer Graphics & Applications, pp. 43-51 (May 1990).

(Continued)

*Primary Examiner*—Andrew W. Johns
*Assistant Examiner*—Patrick Edwards
(74) *Attorney, Agent, or Firm*—Harness, Dickey & Pierce, P.L.C.

(57) ABSTRACT

Apparatus and methods are disclosed for the calibration of a tracked imaging probe for use in image-guided surgical systems. The invention uses actual image data collected from an easily constructed calibration jig to provide data for the calibration algorithm. The calibration algorithm analytically develops a geometric relationship between the probe and the image so objects appearing in the collected image can be accurately described with reference to the probe. The invention can be used with either two or three dimensional image data-sets. The invention also has the ability to automatically determine the image scale factor when two dimensional data-sets are used.

19 Claims, 11 Drawing Sheets

U.S. PATENT DOCUMENTS

| | | | |
|---|---|---|---|
| 4,328,813 A | 5/1982 | Ray | |
| 4,339,953 A | 7/1982 | Iwasaki | 73/654 |
| 4,358,856 A | 11/1982 | Stivender et al. | |
| 4,368,536 A | 1/1983 | Pfeiler | |
| 4,396,885 A | 8/1983 | Constant | |
| 4,396,945 A | 8/1983 | DiMatteo et al. | 358/107 |
| 4,403,321 A | 9/1983 | Kruger | |
| 4,418,422 A | 11/1983 | Richter et al. | |
| 4,419,012 A | 12/1983 | Stephenson et al. | 356/141 |
| 4,422,041 A | 12/1983 | Lienau | 324/207 |
| 4,431,005 A | 2/1984 | McCormick | |
| 4,485,815 A | 12/1984 | Amplatz | |
| 4,543,959 A | 10/1985 | Sepponen | |
| 4,548,208 A | 10/1985 | Niemi | |
| 4,571,834 A | 2/1986 | Fraser et al. | 33/1 PT |
| 4,572,198 A | 2/1986 | Codrington | |
| 4,583,538 A | 4/1986 | Onik et al. | 128/303 B |
| 4,584,577 A | 4/1986 | Temple | |
| 4,613,866 A | 9/1986 | Blood | 343/448 |
| 4,618,978 A | 10/1986 | Cosman | 378/164 |
| 4,621,628 A | 11/1986 | Bludermann | |
| 4,625,718 A | 12/1986 | Olerud et al. | |
| 4,638,232 A * | 1/1987 | Stridsberg et al. | 318/640 |
| 4,642,786 A | 2/1987 | Hansen | 364/559 |
| 4,645,343 A | 2/1987 | Stockdale et al. | |
| 4,649,504 A | 3/1987 | Krouglicof et al. | 364/559 |
| 4,651,732 A | 3/1987 | Frederick | |
| 4,653,509 A | 3/1987 | Oloff et al. | |
| 4,673,352 A | 6/1987 | Hansen | 433/69 |
| 4,706,665 A | 11/1987 | Gouda | |
| 4,719,419 A | 1/1988 | Dawley | |
| 4,722,056 A | 1/1988 | Roberts et al. | 364/413 |
| 4,722,336 A | 2/1988 | Kim et al. | |
| 4,727,565 A | 2/1988 | Ericson | |
| 4,737,794 A | 4/1988 | Jones | 342/448 |
| 4,737,921 A | 4/1988 | Goldwasser et al. | |
| 4,750,487 A | 6/1988 | Zanetti | |
| 4,771,787 A | 9/1988 | Wurster et al. | |
| 4,791,934 A | 12/1988 | Brunnett | |
| 4,793,355 A | 12/1988 | Crum et al. | |
| 4,797,907 A | 1/1989 | Anderton | |
| 4,803,976 A | 2/1989 | Frigg et al. | |
| 4,821,206 A | 4/1989 | Arora | |
| 4,821,731 A | 4/1989 | Martinelli et al. | 128/662.06 |
| 4,836,778 A | 6/1989 | Baumrind et al. | 433/69 |
| 4,845,771 A | 7/1989 | Wislocki et al. | |
| 4,849,692 A | 7/1989 | Blood | 324/208 |
| 4,862,893 A | 9/1989 | Martinelli | |
| 4,889,526 A | 12/1989 | Rauscher et al. | |
| 4,896,673 A | 1/1990 | Rose et al. | 128/660.03 |
| 4,905,698 A | 3/1990 | Strohl, Jr. et al. | |
| 4,923,459 A | 5/1990 | Nambu | 606/130 |
| 4,931,056 A | 6/1990 | Ghajar et al. | |
| 4,945,305 A | 7/1990 | Blood | 324/207.17 |
| 4,945,914 A | 8/1990 | Allen | 128/653 R |
| 4,951,653 A | 8/1990 | Fry et al. | |
| 4,977,655 A | 12/1990 | Martinelli | |
| 4,989,608 A | 2/1991 | Ratner | |
| 4,991,579 A | 2/1991 | Allen | 128/653 R |
| 5,002,058 A | 3/1991 | Martinelli | |
| 5,005,592 A | 4/1991 | Cartmell | |
| 5,013,317 A | 5/1991 | Cole et al. | |
| 5,016,639 A | 5/1991 | Allen | 128/653 R |
| 5,027,818 A | 7/1991 | Bova et al. | |
| 5,030,196 A | 7/1991 | Inoue | |
| 5,030,222 A | 7/1991 | Calandruccio et al. | |
| 5,031,203 A | 7/1991 | Trecha | |
| 5,042,486 A | 8/1991 | Pfeiler et al. | |
| 5,050,608 A | 9/1991 | Watanabe et al. | |
| 5,054,492 A | 10/1991 | Scribner et al. | |
| 5,057,095 A | 10/1991 | Fabian | |
| 5,059,789 A | 10/1991 | Salcudean | 250/206.1 |
| 5,079,699 A | 1/1992 | Tuy et al. | |
| 5,086,401 A | 2/1992 | Glassman et al. | 395/94 |
| 5,094,241 A | 3/1992 | Allen | 128/653.1 |
| 5,097,839 A | 3/1992 | Allen | 128/653.1 |
| 5,099,845 A | 3/1992 | Besz et al. | |
| 5,105,829 A | 4/1992 | Fabian et al. | |
| 5,107,839 A | 4/1992 | Houdek et al. | |
| 5,107,843 A | 4/1992 | Aarnio et al. | |
| 5,107,862 A | 4/1992 | Fabian et al. | |
| 5,109,194 A | 4/1992 | Cantaloube | |
| 5,119,817 A | 6/1992 | Allen | 128/653.1 |
| 5,142,930 A | 9/1992 | Allen et al. | 74/469 |
| 5,152,288 A | 10/1992 | Hoenig et al. | |
| 5,160,337 A | 11/1992 | Cosman | 606/130 |
| 5,161,536 A | 11/1992 | Vikomerson et al. | |
| 5,178,164 A | 1/1993 | Allen | 128/898 |
| 5,178,621 A | 1/1993 | Cook et al. | |
| 5,186,174 A | 2/1993 | Schlondorff et al. | 128/653.1 |
| 5,187,475 A | 2/1993 | Wagener et al. | |
| 5,188,126 A | 2/1993 | Fabian et al. | |
| 5,190,059 A | 3/1993 | Fabian et al. | |
| 5,197,476 A | 3/1993 | Nowacki et al. | |
| 5,197,965 A | 3/1993 | Cherry et al. | |
| 5,198,768 A | 3/1993 | Keren | |
| 5,198,877 A | 3/1993 | Schulz | 356/375 |
| 5,211,164 A | 5/1993 | Allen | 128/653.1 |
| 5,211,165 A | 5/1993 | Dumoulin et al. | |
| 5,211,176 A | 5/1993 | Ishiguro et al. | |
| 5,212,720 A | 5/1993 | Landi et al. | |
| 5,214,615 A | 5/1993 | Bauer | 367/128 |
| 5,219,351 A | 6/1993 | Teubner et al. | |
| 5,222,499 A | 6/1993 | Allen et al. | 128/653.1 |
| 5,228,442 A | 7/1993 | Imran | |
| 5,230,338 A | 7/1993 | Allen et al. | 128/653 |
| 5,233,990 A | 8/1993 | Barnea | |
| 5,237,996 A | 8/1993 | Waldman et al. | |
| 5,249,581 A | 10/1993 | Horbal et al. | 128/664 |
| 5,251,127 A | 10/1993 | Raab | 364/413.13 |
| 5,251,635 A | 10/1993 | Dumoulin et al. | |
| 5,253,647 A | 10/1993 | Takahashi et al. | |
| 5,255,680 A | 10/1993 | Darrow et al. | |
| 5,257,636 A | 11/1993 | White | |
| 5,265,610 A | 11/1993 | Darrow et al. | |
| 5,265,611 A | 11/1993 | Hoenig et al. | |
| 5,269,759 A | 12/1993 | Hernandez et al. | |
| 5,271,400 A | 12/1993 | Dumoulin et al. | |
| 5,273,025 A | 12/1993 | Sakiyama et al. | |
| 5,274,551 A | 12/1993 | Corby, Jr. | |
| 5,279,309 A | 1/1994 | Taylor et al. | 128/782 |
| 5,291,199 A | 3/1994 | Overman et al. | |
| 5,295,483 A | 3/1994 | Nowacki et al. | 128/660 |
| 5,297,549 A | 3/1994 | Beatty et al. | |
| 5,299,254 A | 3/1994 | Dancer et al. | 378/163 |
| 5,299,288 A | 3/1994 | Glassman et al. | 395/80 |
| 5,305,091 A | 4/1994 | Gelbart et al. | |
| 5,305,203 A | 4/1994 | Raab | 364/413.13 |
| 5,309,913 A | 5/1994 | Kormos et al. | 128/653.1 |
| 5,315,630 A | 5/1994 | Sturm et al. | 378/65 |
| 5,316,024 A | 5/1994 | Hirschi et al. | |
| 5,318,025 A | 6/1994 | Dumoulin et al. | |
| 5,320,111 A | 6/1994 | Livingston | |
| 5,325,728 A | 7/1994 | Zimmerman et al. | |
| 5,325,873 A | 7/1994 | Hirschi et al. | |
| 5,329,944 A | 7/1994 | Fabian et al. | |
| 5,333,168 A | 7/1994 | Fernandes et al. | |
| 5,353,220 A | 10/1994 | Ito et al. | 364/413.13 |
| 5,353,795 A | 10/1994 | Souza et al. | |
| 5,353,800 A | 10/1994 | Pohndorf et al. | |
| 5,353,807 A | 10/1994 | DeMarco | |
| 5,357,953 A | 10/1994 | Merrick et al. | 128/633 |
| 5,359,417 A | 10/1994 | Muller et al. | 356/375 |
| 5,368,030 A | 11/1994 | Zinreich et al. | |

| | | | | | |
|---|---|---|---|---|---|
| 5,375,596 A | 12/1994 | Twiss et al. | 5,596,228 A | 1/1997 | Anderton et al. |
| 5,377,678 A | 1/1995 | Dumoulin et al. | 5,600,330 A | 2/1997 | Blood .................. 342/463 |
| 5,383,454 A | 1/1995 | Bucholz .................. 128/653.1 | 5,603,318 A | 2/1997 | Heilbrun et al. ........... 128/630 |
| 5,385,146 A | 1/1995 | Goldreyer | 5,617,462 A | 4/1997 | Spratt |
| 5,385,148 A | 1/1995 | Lesh et al. | 5,617,857 A | 4/1997 | Chader et al. ........... 128/653.1 |
| 5,386,828 A | 2/1995 | Owens et al. | 5,619,261 A | 4/1997 | Anderton |
| 5,389,101 A | 2/1995 | Heilbrun et al. ............ 606/130 | 5,622,169 A | 4/1997 | Golden et al. |
| 5,391,199 A | 2/1995 | Ben-Haim .................. 607/122 | 5,622,170 A | 4/1997 | Schulz .................... 128/653.1 |
| 5,394,457 A | 2/1995 | Leibinger et al. | 5,627,873 A | 5/1997 | Hanover et al. |
| 5,394,875 A | 3/1995 | Lewis et al. ........... 128/660.09 | 5,628,315 A | 5/1997 | Vilsmeier et al. |
| 5,397,329 A | 3/1995 | Allen ........................ 606/73 | 5,630,431 A | 5/1997 | Taylor |
| 5,399,146 A | 3/1995 | Nowacki et al. | 5,636,644 A | 6/1997 | Hart et al. |
| 5,400,384 A | 3/1995 | Fernandes et al. | 5,638,819 A | 6/1997 | Manwaring et al. ...... 128/653.1 |
| 5,402,801 A | 4/1995 | Taylor | 5,640,170 A | 6/1997 | Anderson .................. 343/895 |
| 5,408,409 A | 4/1995 | Glassman et al. ..... 364/413.13 | 5,642,395 A | 6/1997 | Anderton et al. |
| 5,411,026 A | 5/1995 | Carol .................... 128/660.03 | 5,643,268 A | 7/1997 | Vilsmeier et al. |
| 5,417,210 A | 5/1995 | Funda et al. | 5,645,065 A | 7/1997 | Shapiro et al. |
| 5,419,325 A | 5/1995 | Dumoulin et al. | 5,647,361 A | 7/1997 | Damadian |
| 5,423,334 A | 6/1995 | Jordan | 5,662,111 A | 9/1997 | Cosman .................... 128/653.1 |
| 5,425,367 A | 6/1995 | Shapiro et al. | 5,664,001 A | 9/1997 | Tachibana et al. |
| 5,425,382 A | 6/1995 | Golden et al. | 5,674,296 A | 10/1997 | Bryan et al. |
| 5,426,683 A | 6/1995 | O'Farrell, Jr. et al. | 5,676,673 A | 10/1997 | Ferre et al. |
| 5,426,687 A | 6/1995 | Goodall et al. | 5,681,260 A | 10/1997 | Ueda et al. |
| 5,427,097 A | 6/1995 | Depp | 5,682,886 A | 11/1997 | Delp et al. |
| 5,429,132 A | 7/1995 | Guy et al. ................ 128/653.1 | 5,690,108 A | 11/1997 | Chakeres |
| 5,433,198 A | 7/1995 | Desai | 5,694,945 A | 12/1997 | Ben-Haim |
| RE35,025 E | 8/1995 | Anderton | 5,695,500 A | 12/1997 | Taylor et al. |
| 5,437,277 A | 8/1995 | Dumoulin et al. | 5,695,501 A | 12/1997 | Carol et al. |
| 5,443,066 A | 8/1995 | Dumoulin et al. | 5,697,377 A | 12/1997 | Wittkampf |
| 5,443,489 A | 8/1995 | Ben-Haim .................. 607/115 | 5,702,406 A | 12/1997 | Vilsmeier et al. |
| 5,444,756 A | 8/1995 | Pai et al. | 5,711,299 A | 1/1998 | Manwaring et al. |
| 5,445,144 A | 8/1995 | Wodicka et al. | 5,713,946 A | 2/1998 | Ben-Haim |
| 5,445,150 A | 8/1995 | Dumoulin et al. | 5,715,822 A | 2/1998 | Watkins |
| 5,445,166 A | 8/1995 | Taylor | 5,715,836 A | 2/1998 | Kliegis et al. |
| 5,446,548 A | 8/1995 | Gerig et al. ................. 356/375 | 5,718,241 A | 2/1998 | Ben-Haim et al. |
| 5,447,154 A | 9/1995 | Cinquin et al. | 5,727,552 A | 3/1998 | Ryan |
| 5,448,610 A | 9/1995 | Yamamoto et al. | 5,727,553 A | 3/1998 | Saad |
| 5,453,686 A | 9/1995 | Anderson ............... 324/207.17 | 5,729,129 A | 3/1998 | Acker .................... 324/207.12 |
| 5,456,718 A | 10/1995 | Szymaitis | 5,730,129 A | 3/1998 | Darrow et al. ........... 128/653.1 |
| 5,458,718 A | 10/1995 | Venkitachalam | 5,730,130 A | 3/1998 | Fitzpatrick et al. ....... 128/653.1 |
| 5,464,446 A | 11/1995 | Dreessen et al. | 5,732,703 A | 3/1998 | Kalfas et al. ............. 128/653.1 |
| 5,478,341 A | 12/1995 | Cook et al. | 5,735,278 A | 4/1998 | Hoult et al. |
| 5,478,343 A | 12/1995 | Ritter | 5,738,096 A | 4/1998 | Ben-Haim |
| 5,480,422 A | 1/1996 | Ben-Haim .................. 607/122 | 5,741,214 A | 4/1998 | Ouchi et al. |
| 5,483,961 A | 1/1996 | Kelly et al. | 5,742,394 A | 4/1998 | Hansen ....................... 356/375 |
| 5,485,849 A | 1/1996 | Panescu et al. | 5,744,953 A | 4/1998 | Hansen .................. 324/207.17 |
| 5,487,391 A | 1/1996 | Panescu | 5,748,767 A | 5/1998 | Raab .......................... 382/128 |
| 5,487,729 A | 1/1996 | Avellanet et al. | 5,749,362 A | 5/1998 | Funda et al. |
| 5,487,757 A | 1/1996 | Truckai et al. | 5,749,835 A | 5/1998 | Glantz |
| 5,490,196 A | 2/1996 | Rudich et al. | 5,752,513 A | 5/1998 | Acker et al. .............. 128/653.1 |
| 5,494,034 A | 2/1996 | Schlöndorff et al. ..... 128/653.1 | 5,755,725 A | 5/1998 | Druais |
| 5,503,416 A | 4/1996 | Aoki et al. | RE35,816 E | 6/1998 | Schulz ........................ 356/376 |
| 5,513,637 A | 5/1996 | Twiss et al. | 5,758,667 A | 6/1998 | Slettenmark |
| 5,515,160 A | 5/1996 | Schulz et al. ............... 356/241 | 5,762,064 A | 6/1998 | Polvani |
| 5,517,990 A | 5/1996 | Kalfas et al. ............ 128/653.1 | 5,767,669 A | 6/1998 | Hansen et al. .......... 324/207.12 |
| 5,531,227 A | 7/1996 | Schneider | 5,767,960 A | 6/1998 | Orman .................... 356/139.03 |
| 5,531,520 A | 7/1996 | Grimson et al. ............. 382/131 | 5,769,789 A | 6/1998 | Wang et al. ................ 600/414 |
| 5,538,004 A * | 7/1996 | Bamber .................... 600/443 | 5,769,861 A | 6/1998 | Vilsmeier .................... 606/130 |
| 5,542,938 A | 8/1996 | Avellanet et al. | 5,772,594 A | 6/1998 | Barrick ........................ 600/407 |
| 5,543,951 A | 8/1996 | Moehrmann | 5,775,322 A | 7/1998 | Silverstein et al. |
| 5,546,949 A | 8/1996 | Frazin et al. | 5,776,064 A | 7/1998 | Kalfas et al. ................ 600/414 |
| 5,546,951 A | 8/1996 | Ben-Haim .................. 128/702 | 5,782,765 A | 7/1998 | Jonkman |
| 5,551,429 A | 9/1996 | Fitzpatrick et al. | 5,787,886 A | 8/1998 | Kelly et al. |
| 5,558,091 A | 9/1996 | Acker et al. .............. 128/653.1 | 5,792,055 A | 8/1998 | McKinnon |
| 5,568,809 A | 10/1996 | Ben-haim ................... 128/656 | 5,795,294 A | 8/1998 | Luber et al. ................. 600/407 |
| 5,572,999 A | 11/1996 | Funda et al. | 5,797,849 A | 8/1998 | Vesely et al. ................ 600/461 |
| 5,573,533 A | 11/1996 | Strul | 5,799,055 A | 8/1998 | Peshkin et al. ................ 378/42 |
| 5,575,794 A | 11/1996 | Walus et al. | 5,799,099 A | 8/1998 | Wang et al. |
| 5,583,909 A | 12/1996 | Hanover | 5,800,352 A | 9/1998 | Ferre et al. |
| 5,588,430 A | 12/1996 | Bova et al. ............... 128/653.1 | 5,800,535 A | 9/1998 | Howard, III |
| 5,590,215 A | 12/1996 | Allen ........................ 382/128 | 5,802,719 A | 9/1998 | O'Farrell, Jr. et al. |
| 5,592,939 A | 1/1997 | Martinelli ................. 128/653.1 | 5,803,089 A | 9/1998 | Ferre et al. |
| 5,595,193 A | 1/1997 | Walus et al. | 5,807,252 A | 9/1998 | Hassfeld et al. |

| | | | | | | |
|---|---|---|---|---|---|---|
| 5,810,007 A | 9/1998 | Holupka et al. ....... 128/660.03 | | 6,122,538 A | 9/2000 | Sliwa, Jr. et al. |
| 5,810,728 A | 9/1998 | Kuhn | | 6,131,396 A | 10/2000 | Duerr et al. |
| 5,810,735 A | 9/1998 | Halperin et al. | | 6,139,183 A | 10/2000 | Graumann |
| 5,820,553 A | 10/1998 | Hughes ...................... 600/426 | | 6,149,592 A | 11/2000 | Yanof et al. |
| 5,823,192 A | 10/1998 | Kalend et al. | | 6,156,067 A | 12/2000 | Bryan et al. |
| 5,823,958 A | 10/1998 | Truppe ....................... 600/426 | | 6,161,032 A | 12/2000 | Acker |
| 5,828,725 A | 10/1998 | Levinson | | 6,167,296 A | 12/2000 | Shahidi |
| 5,828,770 A | 10/1998 | Leis et al. ................... 382/103 | | 6,172,499 B1 | 1/2001 | Ashe |
| 5,829,444 A | 11/1998 | Ferre et al. | | 6,175,756 B1 | 1/2001 | Ferre et al. |
| 5,831,260 A | 11/1998 | Hansen ....................... 250/221 | | 6,223,067 B1 | 4/2001 | Vilsmeier et al. |
| 5,833,608 A | 11/1998 | Acker | | 6,233,476 B1 | 5/2001 | Strommer et al. |
| 5,834,759 A | 11/1998 | Glossop .................... 250/203.1 | | 6,246,231 B1 | 6/2001 | Ashe |
| 5,836,954 A | 11/1998 | Heilbrun et al. ............ 606/130 | | 6,273,896 B1 | 8/2001 | Franck et al. |
| 5,840,024 A | 11/1998 | Taniguchi et al. | | 6,298,262 B1 | 10/2001 | Franck et al. |
| 5,840,025 A | 11/1998 | Ben-Haim ................... 600/424 | | 6,311,540 B1 * | 11/2001 | Paltieli et al. ............... 73/1.82 |
| 5,843,076 A | 12/1998 | Webster, Jr. et al. | | 6,332,089 B1 | 12/2001 | Acker et al. |
| 5,848,967 A | 12/1998 | Cosman ...................... 600/426 | | 6,341,231 B1 | 1/2002 | Ferre et al. |
| 5,851,183 A | 12/1998 | Bucholz ...................... 600/425 | | 6,351,659 B1 | 2/2002 | Vilsmeier |
| 5,865,846 A | 2/1999 | Bryan et al. | | 6,381,485 B1 | 4/2002 | Hunter et al. |
| 5,868,675 A | 2/1999 | Henrion et al. ............. 600/424 | | 6,415,644 B1 * | 7/2002 | Rockwood et al. .......... 73/1.86 |
| 5,871,445 A | 2/1999 | Bucholz ...................... 600/407 | | 6,424,856 B1 | 7/2002 | Vilsmeier et al. |
| 5,871,455 A | 2/1999 | Ueno | | 6,428,547 B1 | 8/2002 | Vilsmeier et al. |
| 5,871,487 A | 2/1999 | Warner et al. | | 6,434,415 B1 | 8/2002 | Foley et al. |
| 5,873,822 A | 2/1999 | Ferre et al. | | 6,437,567 B1 | 8/2002 | Schenck et al. |
| 5,884,410 A | 3/1999 | Prinz ........................... 33/559 | | 6,445,943 B1 | 9/2002 | Ferre et al. |
| 5,891,034 A | 4/1999 | Bucholz ...................... 600/426 | | 6,470,207 B1 | 10/2002 | Simon et al. |
| 5,891,157 A | 4/1999 | Day et al. | | 6,474,341 B1 | 11/2002 | Hunter et al. |
| 5,904,691 A | 5/1999 | Barnett et al. .............. 606/130 | | 6,493,573 B1 | 12/2002 | Martinelli et al. |
| 5,907,395 A | 5/1999 | Schulz et al. ........... 356/139.03 | | 6,498,944 B1 | 12/2002 | Ben-Haim et al. |
| 5,913,820 A | 6/1999 | Bladen et al. .............. 600/407 | | 6,499,488 B1 | 12/2002 | Hunter et al. |
| 5,920,395 A | 7/1999 | Schulz ........................ 356/375 | | 6,527,443 B1 | 3/2003 | Vilsmeier et al. |
| 5,921,992 A | 7/1999 | Costales et al. ............ 606/130 | | 6,551,325 B1 | 4/2003 | Neubauer et al. |
| 5,923,417 A | 7/1999 | Leis ........................... 356/141.1 | | 6,584,174 B1 | 6/2003 | Schubert et al. |
| 5,923,727 A | 7/1999 | Navab | | 6,609,022 B1 | 8/2003 | Vilsmeier et al. |
| 5,928,248 A | 7/1999 | Acker | | 6,611,700 B1 | 8/2003 | Vilsmeier et al. |
| 5,938,603 A | 8/1999 | Ponzi | | 6,640,128 B1 | 10/2003 | Vilsmeier et al. |
| 5,938,694 A | 8/1999 | Jaraczewski et al. | | 6,694,162 B1 | 2/2004 | Hartlep |
| 5,947,981 A | 9/1999 | Cosman ...................... 606/130 | | 6,701,179 B1 | 3/2004 | Martinelli et al. |
| 5,950,629 A | 9/1999 | Taylor et al. | | | | |
| 5,951,475 A | 9/1999 | Gueziec et al. | | | FOREIGN PATENT DOCUMENTS | |
| 5,954,647 A | 9/1999 | Bova et al. .................. 600/407 | | | | |
| 5,964,796 A | 10/1999 | Imran | | DE | 3042343 A1 | 6/1982 |
| 5,967,980 A | 10/1999 | Ferre et al. | | DE | 3717871 A1 | 12/1988 |
| 5,967,982 A | 10/1999 | Barnett ....................... 600/429 | | DE | 3717871 C2 | 12/1988 |
| 5,968,047 A | 10/1999 | Reed | | DE | 3831278 A1 | 3/1989 |
| 5,971,997 A | 10/1999 | Guthrie et al. .............. 606/130 | | DE | 4225112 C1 | 12/1993 |
| 5,976,156 A | 11/1999 | Taylor et al. | | DE | 4233978 | 4/1994 |
| 5,980,535 A | 11/1999 | Barnett et al. .............. 606/130 | | DE | 19715202 A1 | 10/1998 |
| 5,983,126 A | 11/1999 | Wittkampf | | DE | 19751761 A1 | 10/1998 |
| 5,987,349 A | 11/1999 | Schulz ........................ 600/427 | | DE | 19832296 A1 | 2/1999 |
| 5,987,960 A | 11/1999 | Messner et al. .............. 73/1.79 | | DE | 19747427 A1 | 5/1999 |
| 5,999,837 A | 12/1999 | Messner et al. ............ 600/407 | | DE | 10085137 | 11/2002 |
| 5,999,840 A | 12/1999 | Grimson et al. ............ 600/424 | | EP | 0 155 857 A2 | 9/1985 |
| 6,001,130 A | 12/1999 | Bryan et al. | | EP | 0 319 844 A1 | 1/1988 |
| 6,006,126 A | 12/1999 | Cosman ...................... 600/426 | | EP | 0 326 768 A2 | 8/1989 |
| 6,006,127 A | 12/1999 | Van Der Brug et al. .... 600/427 | | EP | 0419729 A1 | 9/1989 |
| 6,013,087 A | 1/2000 | Adams et al. ............... 606/130 | | EP | 0350996 A1 | 1/1990 |
| 6,016,439 A | 1/2000 | Acker | | EP | 0 359 773 B1 | 3/1990 |
| 6,019,725 A | 2/2000 | Vesely et al. ............... 600/447 | | EP | 0 651 968 A1 | 8/1990 |
| 6,024,695 A | 2/2000 | Taylor et al. | | EP | 0 456 103 A2 | 11/1991 |
| 6,035,228 A | 3/2000 | Yanof et al. ................. 600/429 | | EP | 0 469 966 A1 | 2/1992 |
| 6,050,724 A | 4/2000 | Schmitz et al. | | EP | 0 581 704 B1 | 7/1993 |
| 6,052,611 A | 4/2000 | Yanof et al. ................. 600/429 | | EP | 0894473 A2 | 1/1995 |
| 6,059,718 A | 5/2000 | Taniguchi et al. | | EP | 0 655 138 B1 | 5/1995 |
| 6,061,644 A | 5/2000 | Leis ............................ 702/153 | | EP | 0 904 735 A2 | 3/1999 |
| 6,063,022 A | 5/2000 | Ben-Haim | | EP | 0 908 146 A2 | 4/1999 |
| 6,069,932 A | 5/2000 | Peshkin et al. ............... 378/42 | | EP | 0 950 380 A1 | 10/1999 |
| 6,073,043 A | 6/2000 | Schneider | | FR | 2417970 | 2/1979 |
| 6,073,044 A | 6/2000 | Fitzpatrick et al. .......... 600/426 | | JP | 2765738 | 6/1998 |
| 6,076,008 A | 6/2000 | Bucholz ...................... 600/427 | | WO | WO 88/09151 | 12/1988 |
| 6,101,455 A * | 8/2000 | Davis ........................... 702/94 | | WO | WO 89/05123 | 6/1989 |
| 6,104,944 A | 8/2000 | Martinelli | | WO | WO 91/03982 | 4/1991 |
| 6,118,845 A | 9/2000 | Simon et al. | | WO | WO 91/04711 | 4/1991 |

| | | |
|---|---|---|
| WO | WO 91/07726 | 5/1991 |
| WO | WO 92/03090 | 3/1992 |
| WO | WO 92/06645 | 4/1992 |
| WO | WO 94/04938 | 3/1994 |
| WO | WO 9404938 | 3/1994 |
| WO | WO 94/23647 | 10/1994 |
| WO | WO 94/24933 | 11/1994 |
| WO | WO 95/07055 | 3/1995 |
| WO | WO 96/08209 | 3/1996 |
| WO | WO 96/11624 | 4/1996 |
| WO | WO 96/32059 | 10/1996 |
| WO | WO 97/36192 | 10/1997 |
| WO | WO 97/49453 | 12/1997 |
| WO | WO 98/08554 | 3/1998 |
| WO | WO 98/38908 | 9/1998 |
| WO | WO 99/15097 | 4/1999 |
| WO | WO 99/21498 | 5/1999 |
| WO | WO 99/23956 | 5/1999 |
| WO | WO 99/26549 | 6/1999 |
| WO | WO 99/27839 | 6/1999 |
| WO | WO 99/29253 | 6/1999 |
| WO | WO 99/33406 | 7/1999 |
| WO | WO 99/38449 | 8/1999 |
| WO | WO 99/52094 | 10/1999 |
| WO | WO 99/56654 | 11/1999 |
| WO | WO 99/60939 | 12/1999 |
| WO | WO 00/10456 | 3/2000 |
| WO | WO 01/30437 A1 | 5/2001 |

OTHER PUBLICATIONS

Adams, L., et al., *Aide au Reperage Tridimensionnel pour la Chirurgie de la Base du Crane,* Innov. Tech. Biol. Med., vol. 13, No. 4, pp. 409-424 (1992).

Arun, K.S., et al., *Least-Squares Fitting of Two 3-D Point Sets,* IEEE Transactions on Pattern Analysis and Machine Intelligence, vol. PAMI-9, No. 5, pp. 698-700 (Sep. 1987).

Benzel, E., et al., *Magnetic Source Imaging: A Review of the Magnes System of Biomagnetic Technologies Incorpora*ted, Neurosurgery, vol. 33, No. 2, (Aug. 1993).

Bergstrom, M., et al., *Stereotaxic Computed Tomography,* Am. J. Roentgenol, vol. 127 pp. 167-170 (1976).

Boethius, J., et al., *Stereotactic Biopsies and Computer Tomography in Gliomas,* Acta Neurochirurgica, vol. 40, pp. 223-232 (1978).

Bopp, H., et al., *An Orientation and Calibration Method for Non-Topographic Applications,* Photogrammetric Engineering and Remote Sensing, vol. 44, No. 9, pp. 1191-1196 (Sep. 1978).

Bucholz, R.D., et al., *Variables affecting the accuracy of stereotatic localization using computerized tomography,* J. Neurosurg., vol. 79, pp. 667-673 (1993).

Bucholz, R.D., et al., *A Comparison of Sonic Digitizers Versus Light Emitting Diode-Based Localization,* Interactive Image-guided Neurosurgery, Chapter 16, pp. 179-200 (1993).

Bucholz, R.D., et al., *Intraoperative localization using a three dimensional optical digitizer,* SPIE-The Intl. Soc. for Opt. Eng., vol. 1894, pp. 312-322 (Jan. 17-19, 1993).

Bucholz, R.D., et al., *Image-guided surgical techniques for infections and trauma of the central nervous system,* Neurosurg. Clinics of N.A., vol. 7, No. 2, pp. 187-200 (1996).

Bucholz, R.D., et al., *The Correction of Stereotactic Inaccuracy Caused by Brain Shift Using an Intraoperative Ultrasound Device,* First Joint Conference, Computer Vision, Virtual Reality and Robotics in Medicine and Medical Robotics and Computer-Assisted Surgery, Grenoble, France, pp. 459-466 (Mar. 19-22, 1997).

Bucholz, R.D., et al., *Intraoperative Ultrasonic Brain Shift Monitor and Analysis,* Stealth Station Marketing brochure (undated).

Champleboux, G., et al., *Accurate Calibration of Cameras and Range Imaging Sensors: the NPBS Method,* Proceedings of the 1992 IEEE Int'l Conf. on Robotics and Automation, Nice, France (May 1992).

Cinquin, P., et al., *Computer Assisted Medical Interventions,* IEEE, pp. 254-263 (May/Jun. 1995).

Clarysse, P., et al., *A Computer-Assisted System for 3-D Frameless Localization in Stereotaxic MRI,* IEEE Trans. on Med. Imaging, vol. 10, No. 4, pp. 523-529 (Dec. 1991).

Davatzikos, C., et al., *Brain Image Registration Based on Curve Mapping,* IEEE, pp. 245-254 (1994).

Foley, K.T., et al., *Image-guided spine surgery utilizing frameless stereotaxy,* Comparison and analysis (stamped confidential, undated).

Foley, K.T., et al., *Image-guided Intraoperative Spinal Localization,* Intraoperative Neuroprotection, Chapter 19, pp. 325-340 (1996).

Foley, K.T., et al., *The StealthStation™: Three-Dimensional Image-Interactive Guidance for the Spine Surgeon,* Spinal Frontiers, pp. 7-9 (Apr. 1996).

Friets, E.M., et al., *A Frameless Stereotaxic Operating Microscope for Neurosurgery,* IEEE Trans. on Biomed. Eng., vol. 36, No. 6, pp. 608-617 (1989).

Gallen, C.C., et al., *Intracranial Neurosurgery Guided by Functional Imaging,* Surg. Neurol., vol. 42, pp. 523-530 (1994).

Germano, Isabelle M., et al., *The NeuroStation System for Image-Guided, Frameless stereotaxy,* Neurosurg., vol. 37, No. 2, pp. 348-350 (Aug. 1995).

Gomez, C.R., et al., *Transcranial Doppler Ultrasound Following Closed Head Injury: Vasospasm or Vasoparalysis?,* Surg. Neurol., vol. 35, pp. 30-35 (1991).

Gottesfeld Brown, L.M., et al., *Registration of Planar Film Radiographs with Computed Tomography,* IEEE, Proceedings of MMBIA '96, pp. 42-51 (1996).

Gramkow, C., *Registration of 2D and 3D Medical Images,* pp. 1-327 (complete book) (1996).

Grimson, W.E.L., et al., *Virtual-reality technology is giving surgeons the equivalent of x-ray vision helping them to remove tumors . . . ,* Sci. Amer., vol. 280, No. 6, pp. 62-69 (Jun. 1999).

Guéziec, A.P., et al., *Registration of Computed Tomography Data to a Surgical Robot Using Fluoroscopy: A Feasibility Study,* Computer Science/Mathematics, RC 20561, 6 pages (Sep. 27, 1996).

Hamadeh, A., et al., *Towards automatic registration between CT and X-ray images: cooperation between 3D/2D registration and 2D edge detection,* TIMC-IMAG, Faculté de Medecine de Grenoble, France, pp. 39-46 (1995)(Second Annual Intl. Symposium on Medical Robotics and Computer-Assisted Surgery, MRCAS '95, Nov. 4-7, 1995).

Hamadeh, A., et al., *Kinematic Study of Lumbar Spine Using Functional Radiographies and 3D / 2D Registration,* First Joint Conference Computer Vision, Virtual Reality and Robotics in Medicine and Medical Robotics and Computer-Assisted Surgery, Grenoble, France (Mar. 19-22, 1997).

Hamadeh, A., et al., *Automated 3-Dimensional Computer Tomographic and Fluoroscopic Image Registration,* Computer Aided Surgery, vol. 3, pp. 11-19 (1998).

Hatch, J.F., *Reference-Display System for the Integration of CT Scanning and the Operating Microscope,* IEEE, vol. 8, pp. 252-254, Proceedings of the Eleventh Annual Northeast Bioengineering Conference (Worcester, Massachusetts) (Mar. 14-15, 1985).

Heilbrun, M.P., *Computed Tomography-Guided Stereotactic Systems,* Clinical Neurosurgery, Chapter 31, pp. 564-581 (1983).

Heilbrun, M.P., et al., *Preliminary Experience with Brown-Roberts-Wells (BRW) computerized tomography stereotaxic guidance system,* J. Neurosurg., vol. 59, pp. 217-222 (1983).

Heilbrun, M.P., et al., *Stereotactic localization and Guidance Using a Machine Vision Technique,* Stereotact. Funct. Neurosurg., Proceed. of the Mtg. of the Amer. Soc. for Stereot. and Funct. Neurosurg. (Pittsburgh, PA) vol. 58, pp. 94-98 (1992).

Heilbrun, M.P., *Progressive Technology Applications,* Neurosurgery for the Third Millenium, Chapter 15, pp. 191-198 (1992) (J. Whitaker & Sons Ltds., Amer. Assoc. of Neurol. Surgeons, Oct. 1992).

Henderson, J.M., et al., *An Accurate and Ergonomic Method of Registration for Image-guided Neurosurgery,* Computerized Medical Imaging and Graphics, vol. 18, No. 4, pp. 273-277 (1994).

Hofstetter, R., et al., *Fluoroscopy Based Surgical Navigation-Concept and Clinical Applications,* Computer Assisted Radiology and Surgery, CAR '97, Proceed. of the 11$^{th}$ Intl. Symp. and Exh., Berlin, pp. 956-960 (Jun. 25-28, 1997).

Horn, B.K., *Closed-form solution of absolute orientation using unit quaternions,* Optical Society of America, vol. 4, No. 4, pp. 629-642 (Apr. 1987).

Horner, N.B., et al., *A Comparison of CT-Stereotaxic Brain Biopsy Techniques,* Investig. Radiol., vol. 19, pp. 367-373 (Sep.-Oct. 1984).

Kato, A., et al., *A frameless, armless navigational system for computer-assisted neurosurgery,* J. Neurosurg., vol. 74, pp. 845-849 (May 1991).

Klimek, L., et al., *Long-Term Experience with Different Types of Localization Systems in Skull-Base Surgery,* Ear, Nose & Throat Surgery, Chapter 51, pp. 635-638 (undated).

Kosugi, Y., et al., *An Articulated Neurosurgical Navigation System Using MRI and CT Images,* IEEE Trans. on Biomed. Eng., vol. 35, No. 2, pp. 147-152 (Feb. 1988).

Krybus, W., et al., *Navigation Support for Surgery by Means of Optical Position Detection,* Computer Assisted Radiology Proceed. of the Intl. Symp. CAR '91 Computed Assisted Radiology, pp. 362-366 (Jul. 3-6, 1991).

Lavallée, S., et al., *A new system for computer assisted neurosurgery,* IEEE EMBS, 11$^{th}$ Annual Intl. Conf., pp. 926-927 (1989).

Lavallée, S., et al., *Computer Assisted Interventionist Imaging: The Instance of Stereotactic Brain Surgery,* MEDINFO 89, pp. 613-617 (1989).

Lavallée, S., et al., *Computer Assisted Medical Interventions,* NATO ASI Series, vol. F 60, 3D Imaging in Medic., pp. 301-312 (1990).

Lavallée, S., et al., *Matching 3-D Smooth Surfaces with their 2-D Projections using 3-D Distance Maps,* SPIE Geometric Methods in Computer Vision, vol. 1570, pp. 322-336 (1991).

Lavallée, S., et al., *Matching of Medical Images for Computed and Robot Assisted Surgery,* Annual Int'l Conf. of the IEEE Engineering in Medic. and Biol. Society, vol. 13, No. 1, pp. 39-40 (1991).

Lavallée, S., et al., *Image guided operating robot: a clinical application in stereotactic neurosurgery,* IEEE Rob. and Autom. Society, Proc. of the 1992 Intl. Conf. on Rob. and Autom., May 1992, pp. 618-624, First Intl. Symp. on Med. Rob. and Comp. Assisted Surg. (Pittsburgh, PA) (Sep. 22-24, 1994).

Lavallée, S., et al., *Computer Assisted Spine Surgery: a technique for accurate transpedicular screw fixation,* TIMC, Faculté de Medecine de Grenoble, J. of Image Guided Surg., vol. 1, No. 1, pp. 65-73 (1995).

Leavitt, D.D., et al., *Dynamic Field Shaping to Optimize Stereotactic Radiosurgery,* I.J. Rad. Onc. Biol. Phys., vol. 21, pp. 1247-1255 (1991).

Merloz, P., et al., *Computer assisted Spine Surgery,* Clinical Orthop. and Related Research, No. 337, pp. 86-96 (1997).

Pelizzari, C.A., et al., *Interactive 3-D Patient—Image Registration,* Lecture Notes in Computer Science, Information Processing in Medical Imaging,12th Int'l Conf., IPMI, pp. 132-141 (Jul. 1991).

Pelizzari, C.A., et al., *Accurate Three-Dimensional Registration of CT, PET, and/or MR Images of the Brain,* Journal of Computer Assisted Tomography, vol. 13, No. 1, pp. 20-26 (Jan./Feb. 1989).

Penn, R.D., et al., *Stereotactic Surgery with Image Processing of Computerized Tomographic Scans,* Neurosurgery, vol. 3, No. 2, pp. 157-153 (Sep.-Oct. 1978).

Potamianos, P., et al., *Intra-Operative Imaging Guidance for Keyhole Surgery Methodology and Calibration,* MRCAS, pp. 98-104 (1994).

Potamianos, P., et al., *Intra-Operative Registration for Percutaneous Surgery,* MRCAS, pp. 156-164 (1995).

Reinhardt, H.F., et al., *Intraoperative CT-Correlated Localization of Brain Tumors,* European Surgical Research, Jan.-Feb. issue, pp. 52-58 (1988).

Reinhardt, H.F., et al., *Interactive Sonar-Operated Device for Stereotactic and Open Surgery),* Proceedings of the 10$^{th}$ Meeting of the World Society for Stereotactic and Functional Neurosurgery, Maebashi, Japan, pp. 393-397 (Oct. 1989).

Reinhardt, H.F., et al., *Mikrochirurgische Entfernung . . . (Microsurgical removal of Deep-Seated Vascular Malformations Using Sonar Stereometry),* Ultraschall in Med. 12, pp. 80-83 (1991).

Reinhardt, Hans F., *Neuronavigation: A Ten-Year Review,* Neurosurgery, pp. 329-341 (undated).

Reinhardt, H.F., et al., *Sonic Stereometry in Microsurgical Procedures for Deep-Seated Brain Tumors and Vascular Malformations,* Neurosurgery, vol. 32, No. 1, pp. 51-57 (Jan. 1993).

Roberts, D.W., et al., *A frameless stereotaxic integration of computerized tomographic imaging and the operating microscope,* J. Neurosurg., vol. 65, pp. 545-549 (Oct. 1986).

Saw, C.B., et al., *Coordinate transformations and calculation of the angular and depth parameters for a stereotactic system,* Medical Physics, vol. 14, No. 6, pp. 1042-1044 (Nov./Dec. 1987).

Shiu, Y.C., et al., *Finding the Mounting Position of a Sensor by Solving a Homogeneous Transform Equation of the Form AX=XB,* IEEE Int'l Conf. on Robotics and Automation, vol. 3, pp. 1666-1671 (1987).

Simon, D.A., et al., *Accuracy Validation in Image-Guided Orthopaedic Surgery,* Second Annual Intl. Symp. on Med. Rob. and Comp.-Assisted Surgery, MRCAS '95, pp. 185-192 (1995).

Smith, K.R., et al., *The NEUROSTATION™—A highly accurate, minimally invasive solution to frameless sterotactic neurosurgery,* Comp. Med. Imaging and Graphics, vol. 18, No. 4, pp. 247-256 (1994).

Smith, K.R., et al., *Multimodality Image Analysis and Display Methods for Improved Tumor Localization in Stereotactic Neurosurgery,* Annual Intl. Conf. of the IEEE Eng. in Med. and Biol. Soc., vol. 13, No. 1, p. 210 (1991).

Smith, K.R., et al., *Computer Methods for Improved Diagnostic Image Display Applied to Stereotactic Neurosurgery,* Automedical, vol. 14, pp. 371-386 (1991).

Weese, J., et al., An Approach to 2D/3D Registration of a Vertebra in 2D X-ray Fluoroscopies with 3D CT Images, CVRMed-MRCAS '97, First Joint Conf., Computer Vision, Virtual Reality and Robotics Medicine and Medical Robotics and Computer-Assisted Surgery, Grenoble, France, pp. 119-128 (1997).

*Stereotactic One, Affordable PC Based Graphics for Stereotactic Surgery,* Stereotactic Image Systems, Inc. (SLC, Utah) (marketing brochure, undated).

BrainLab marketing brochures for Vector Vision (undated).

*The Laitinen Stereoadapter 5000, Instructions for use,* by Surgical Navigation Technologies, FDA-NS-001A Rev. 0 (undated).

*Pixsys 3-D Digitizing Accessories,* by Pixsys (marketing brochure, undated).

"Prestige Cervical Disc System Surgical Technique", 12 pgs.

Adams et al., "Orientation Aid for Head and Neck Surgeons," Innov. Tech. Biol. Med., vol. 13, No. 4, 1992, pp. 409-424.

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 4, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedic Surgery," CAR '98, pp. 716-722.

Bryan, "Bryan Cervical Disc System Single Level Surgical Technique", Spinal Dynamics, 2002, pp. 1-33.

Champleboux, "Utilisation de Fonctions Splines pour la Misa au Point D'un Capteur Tridimensionnel sans Contact," Quelques Applications Medicales, Jul. 1991.

Cinquin et al., "Computer Assisted Medical Interventions," International Advanced Robotics Programme, Sep. 1989, pp. 63-65.

Feldmar et al., "3D-2D Projective Registration of Free-Form Curves and Surfaces," Rapport de recherche (Inria Sophia Antipolis), 1994, pp. 1-44.

Foley et al., "Fundamentals of Interactive Computer Graphics," The Systems Programming Series, Chapter 7, Jul. 1984, pp. 245-266.

Gildenberg et al., "Calculation of Stereotactic Coordinates from the computed Tomographic Scan," Neurosurgery, vol. 10, No. 5, May 1982, pp. 580-586.

Gonzalez, "Digital Image Fundamentals," Digital Image Processing, Second Edition, 1987, pp. 52-54.

Hatch, "Reference-Display System for the Integration of CT Scanning and the Operating Microscope," Thesis, Thayer School of Engineering, Oct. 1984, pp. 1-189.

Hoerenz, "The Operating Microscope I. Optical Principles, Illumination Systems, and Support Systems," Journal of Microsurgery, vol. 1, 1980, pp. 364-369.

Hounsfield, "Computerized transverse axial scanning (tomography): Part 1. Description of system," British Journal of Radiology, vol. 46, No. 552, Dec. 1973, pp. 1016-1022.

Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.

Jacques et al., "Computerized three-dimensional stereotaxic removal of small central nervous system lesion in patients," J. Neurosurg., vol. 53, Dec. 1980, pp. 816-820.

Joskowicz et al., "Computer-Aided Image-Guided Bone Fracture Surgery: Concept and Implementation," CAR '98, pp. 710-715.

Kelly et al., "Computer-assisted stereotaxic laser resection of intra-axial brain neoplasms," Journal of Neurosurgery, vol. 64, Mar. 1986, pp. 427-439.

Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.

Laitinen et al., "An Adapter for Computer Tomography-Guided, Stereotaxis," Surg. Neurol., 1985, pp. 559-566.

Laitinen, "Noninvasive multipurpose stereoadapter," Neurological Research, Jun. 1987, pp. 137-141.

Lavallee et al., "Computer Assisted Driving of a Needle into the Brain," Proceedings of the International Symposium CAR '89, Computer Assisted Radiology, 1989, pp. 416-420.

Lavallee, "VI Adaption de la Methodologie a Quelques Applications Cliniques," Chapitre VI, pp. 133-148.

Leksell et al., "Stereotaxis and Tomography—A Technical Note," ACTA Neurochirurgica, vol. 52, 1980, pp. 1-7.

Lemieux et al., "A Patient-to-Computed-Tomography Image Registration Method Based on Digitally Reconstructed Radiographs," Med. Phys. 21 (11), Nov. 1994, pp. 1749-1760.

Levin et al., "The Brain: Integrated Three-dimensional Display of MR and PET Images," Radiology, vol. 172, No. 3, Sep. 1989, pp. 783-789.

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.

Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.

Pelizzari et al., No. 528—"Three Dimensional Correlation of PET, CT and MRI Images," The Journal of Nuclear Medicine, vol. 28, No. 4, Apr. 1987, p. 682.

Phillips et al., "Image Guided Orthopaedic Surgery Design and Analysis," Trans Inst. MC, vol. 17, No. 5, 1995, pp. 251-264.

Reinhardt et al., "CT-Guided 'Real Time' Stereotaxy," ACTA Neurochirurgica, 1989.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

The Laitinen Stereotactic System, E2-E6.

Viant et al., "A Computer Assisted Orthopaedic System for Distal Locking of Intramedullary Nails," Proc. of MediMEC '95, Bristol, 1995, pp. 86-91.

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Merloz, et al., "Computer Assisted Spine Surgery", Clinical Assisted Spine Surgery, No. 337, pp. 86-96.

Hatch, et al., "Reference-Display System for the Integration of CT Scanning and the Operating Microscope", Proceedings of the Eleventh Annual Northeast Bioengineering Conference, Mar. 14-15, 1985, pp. 252-254.

* cited by examiner

SYSTEM AND METHOD FOR IMAGE BASED SENSOR CALIBRATION

BACKGROUND OF THE INVENTION

1. Field of Invention

The present invention is directed generally to image guided medical systems, and more particularly, to systems and methods for utilizing data collected from imaging sensors to calibrate a tracking device.

2. Description of the Related Art

Image guided surgical techniques have been used with success in aiding physicians for performing a wide variety of delicate surgical procedures. These systems are typically used when the visualization of a surgical tool could be obscured by a patient's anatomy, or when the surgical tool is visible but the patient's anatomy could be difficult to visualize.

In order for these systems to be effective, points of the patient's anatomy appearing in the image must be accurately correlated to the instrument being tracked by the surgical navigation system. Accomplishing this correlation requires the accurate calibration of the tracking device. Ultimately, the calibration problem involves determining the position and orientation (POSE) of a set of points displayed by the image plane in the space defined by the tracking markers of the tracked instrument. It can be assumed that the structure associated with the tracking markers and image plane is a rigid body, so once the POSE is determined it remains constant. However, it is not possible to physically measure the POSE of the points in the image plane.

In addition to being robust and accurate, a preferred calibration scheme must be an uncomplicated procedure which can be performed quickly in the field by minimally trained personnel.

SUMMARY OF THE INVENTION

The present invention is directed generally to image guided medical systems, ERSON, and, particularly, to systems which correlate tracked instrument positions to image data obtained from a patient. More specifically, the present invention is directed to a device and method for registering tracking device outputs with image data.

To achieve these objects and other advantages and in accordance with the purpose of the invention, as embodied and broadly described herein, the invention is directed to an apparatus and method for determining the calibration of a tracking device using image data collected by a tracked probe.

In one aspect of the invention, a surgical navigation system performs the tracking of a position of a calibration jig and a position of a probe. An imaging system performs the collection of a plurality of images of at least one calibration pattern contained in the calibration jig. After receiving the images from the imaging system, the navigation system locates the centers of intersection points in image space associated with each calibration pattern for each of the plurality of images, and extracts a calibration point therefrom. The navigation system then determines the three-dimensional position for at least one calibration point in probe space for each of the plurality of images. Furthermore, the navigation system then relates the positions of the calibration points in image space and the positions of the calibration points in probe space with a coordinate transform. Using this coordinate transform, the navigation system computes a reference position of the image in probe space and stores this reference position. Once the coordinate transform and image reference position in probe space are obtained, the calibration process is complete.

In another aspect of the invention, a surgical navigation system performs the tracking of a position of a calibration jig and a position of a probe. A three-dimensional imaging system performs the collection of a volumetric image of at least one calibration pattern contained in the calibration jig. After receiving the volumetric image from the imaging system, the navigation system extracts two-dimensional slices from the volumetric image and locates centers of intersection points in slice space associated with each calibration pattern for each of the plurality of slices, and extracts a calibration point therefrom. The navigation system then determines the three-dimensional position for at least one calibration point in probe space for each of the plurality of slices. Furthermore, the navigation system then relates the positions of the calibration points in slice space and the positions of the calibration points in probe space with a coordinate transform. Using this coordinate transform, the navigation system computes and stores a reference position of the volumetric image in probe space. Once the coordinate transform and volumetric image reference position in probe space are obtained, the calibration process is complete.

The invention allows for accurate, free-hand calibration of a tracked instrument which can be performed by minimally trained personnel. The calibration jig may be a sterile object and used within an operating room prior to the performance of a surgical procedure. Furthermore, problems associated with the calibration jig or the imaging system can easily be detected by inspection of the images as the calibration is being performed.

It is to be understood that both the foregoing general description and the following detailed description are exemplary only and are not intended to be restrictive of the invention.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 2b depicts a top view of the calibration jig shown in FIG. 2a.

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

Figure 1:
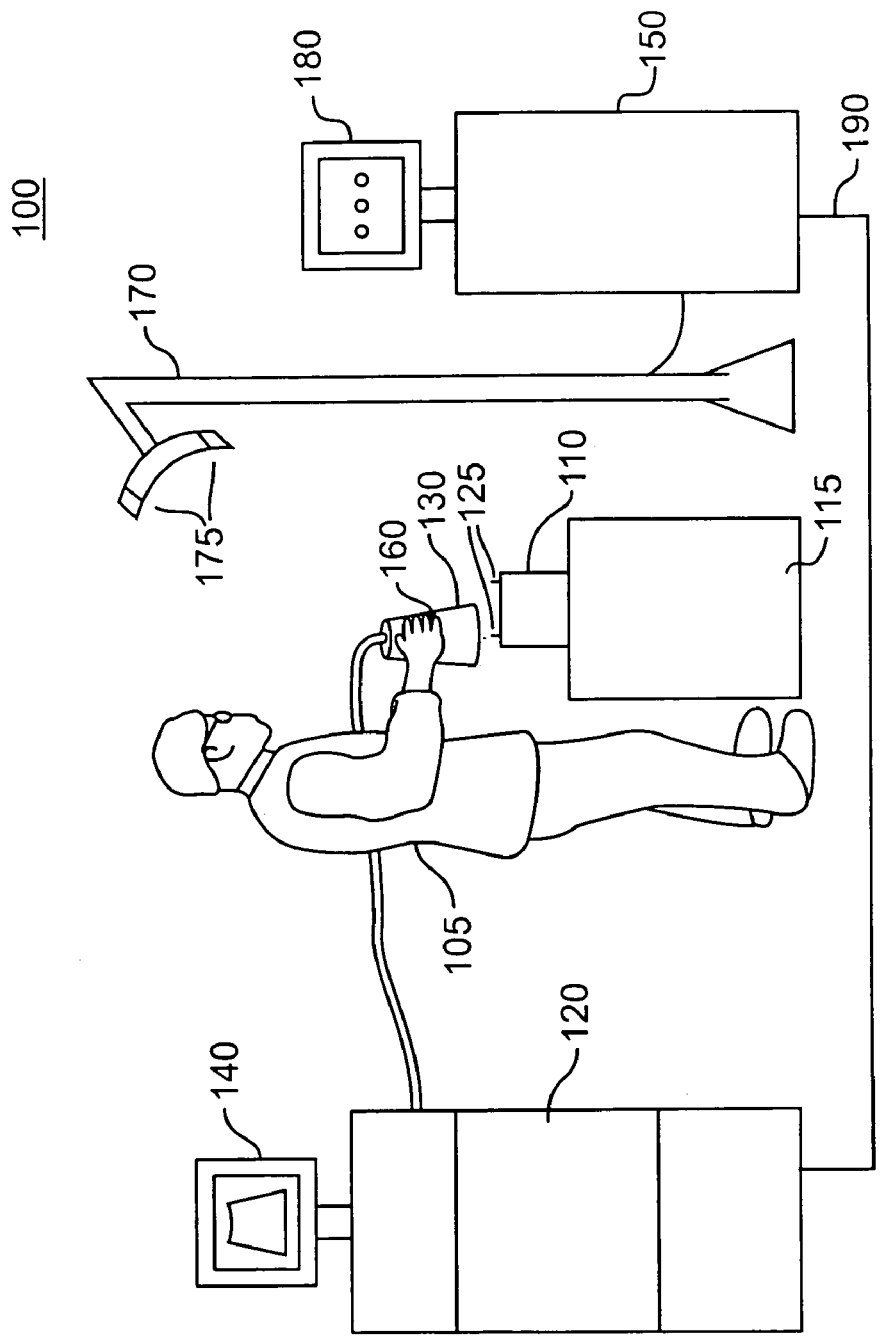
FIG. 1 is a simplified side view of an embodiment of a system for the calibration of a probe in accordance with the present invention.

FIG. 1 illustrates an exemplary calibration system and method 100 which is consistent with the present invention. Stationary calibration jig 110 supported by platform 115 is scanned by technician 105 by manipulating probe 130. Probe 130 comprises a transducer which transmits signals in the direction of the jig 110. Signals reflected from jig 110 can then be received by probe 130 and fed by cable to imaging system 120. Imaging system 120 processes the received signals and forms images which can be displayed on monitor 140. In the preferred embodiment imaging system 120 is a standard ultrasonic imaging system; however, it should be appreciated that other types of imaging systems, such as microwave, X-ray, or optical could also be used with the present invention. Probe 130 typically is tracked, and for example, has a plurality of tracking markers 160 or other trackable features attached at its distal end. Additionally, calibration jig 110 can also have a plurality of tracking markers 125 attached to its surface. In the preferred embodiment, markers 125 can be attached to the periphery of the upper surface of calibration jig 110.

Tracking markers 125 and 160 can include by way of example only reflectors/emitters operating in the optical, infrared, electromagnetic, and/or acoustic domains and/or other suitable devices known in the art. For example, tracking markers such as those supplied by Northern Digital Incorporated may be used in conjunction with the present invention. It should be noted that the jig calibration markers 125 do not have to be identical to the probe calibration markers 160.

The tracking markers can be used to localize probe 130 and calibration jig 110. Localization is the process of determining the position and orientation of an object of interest and tracking movement of the object over some period of observation.

The manner in which sensor 170 tracks the positions of calibration jig 110 and probe 130 is well known in the art and is therefore only described generally. Sensor 170 comprises a detector array 175 which can be used to detect energy from the tracking markers 125 and 160. In the preferred embodiment, the array is a set of CCD cameras which sense infrared energy. However, other sensors may be used which operate at acoustic, electromagnetic, optical, radiological, and/or other frequencies. For example, sensor array 175 is located and suspended by a mount in such a manner as to provide a line of sight between the mount and tracking markers 125 and 160. Signals from sensor 170 are coupled into computer 150 which processes the received data to determine the position of the markers and, consequently the position of the object attached thereto. Based on the relative positions of the markers as sensed in detector array, the positions of objects can be determined and representations of the objects can be displayed on monitor 180. The tracking technology employed in the present invention may be the same as that used in the STEALTH STATION® Treatment Guidance Platform available from Medtronic Sofamor Danek, Inc.

Surgical navigation systems which perform localization functions to assist in medical procedures are well established. Such systems are disclosed, for example, in PCT Application No. PCT/US95/12894 (Publication No. WO 96/11624) to Bucholz, the entire disclosure of which is incorporated by reference.

Referring further to FIG. 1, imaging machine 120 is coupled to computer 150 through suitable link or connection 190. Connection 190 may be, for example, a device specific digital interface or a generic video output signal. Image data from this connection may be used by computer 150 to perform the calculations required to calibrate the tracking of probe 130. Images taken by probe 130 have specific characteristics due to the construction of the calibration jig 110. These characteristics, which are geometric in nature and will be described in detail later, can be used to determine the position of points appearing in the image in a coordinate system referenced to calibration jig 110. The space defined by the coordinate system referenced to jig 110 is termed jig space for purposes of this document. Since the surgical navigation system is tracking the calibration jig, navigation system computer 150 can also determine the positions of the calibration points in a coordinate system referenced to the probe, defined as probe space for purposes of this document. Positions of these same calibration points are also measured in the image coordinate system, or image space, which typically are measured in pixels. By utilizing the positions of the same calibration points described in the both image space and probe space, a relationship between the spaces can be derived. Once this relationship is determined, any pixel in the image can be accurately described in probe space, and thus the calibration will be complete.

Furthermore, although FIG. 1 shows a single computer 150 performing the localization and calibration functions, multiple computers may be implemented as a single computer to perform the functions performed by computer 150. Although a STEALTH STATION® image guided system manufactured by Medtronic Sofamor Danek has been identified, it will be appreciated that the present invention may be utilized with other types of computer systems. In addition, even though FIG. 1 shows only one display 180 coupled to computer 150, multiple displays of various types known in the art may be coupled to computer 150 in order to provide information to the user of the system.

Figure 2A:
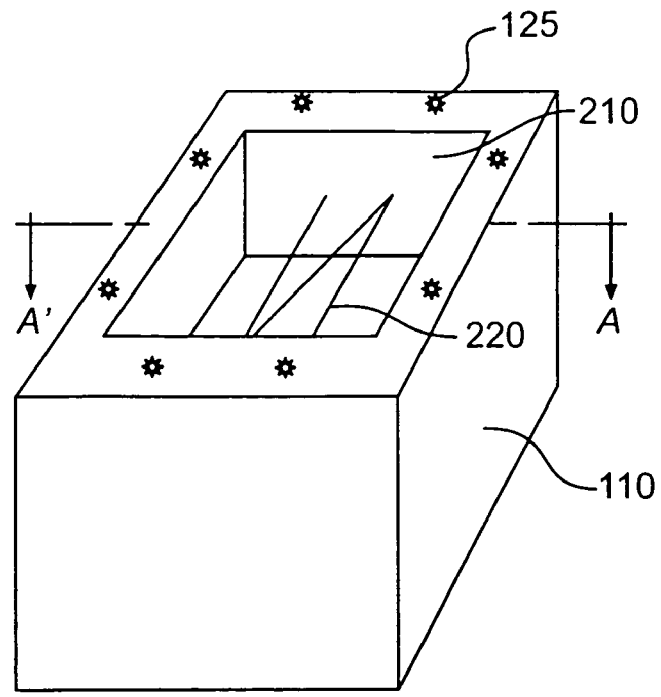
FIG. 2a is a perspective view of an embodiment of a calibration jig in accordance with the present invention.

FIG. 2a shows a perspective view of calibration jig 110. In the preferred embodiment, a plurality of tracking markers 125 can be attached around the perimeter of the jig's upper surface so the jig may be localized by the surgical navigation system. The calibration jig contains a structure which includes a calibration pattern. In general, the calibration pattern may include of a plurality of parallel members joined by a common member. The geometric relationship between the common member and the parallel members is preferably known and well controlled. The calibration pattern in its most basic form can include a set of wires 220 with a diameter comparable to the wavelength of the radiation from the imaging device. The set of wires may be arranged in a "Z" pattern as shown in the FIG. 2a. The mounting points of the two parallel wires within the "Z" pattern is preferably known in calibration jig space at least to the precision desired by the calibration process. While only one "Z" pattern is shown in FIG. 2a and in subsequent figures for purposes of clarification, it should be appreciated that a plurality of "Z" patterns may be contained within calibration jig 110. It should be understood that other suitable patterns can also be used.

For the preferred embodiment, wires 220 may be constructed of nylon and are submerged in a suitable homogenous imaging medium 210 having a known value for the velocity of propagation of the ultrasound wave emitted by the probe. Such a medium, for example, may be water, ultrasound gel, or some other substance which approximates wave propagation through a biological organism. Images of the "Z" pattern are preferably collected with the imager as perpendicular to the plane formed by the "Z" pattern.

Figure 2B:
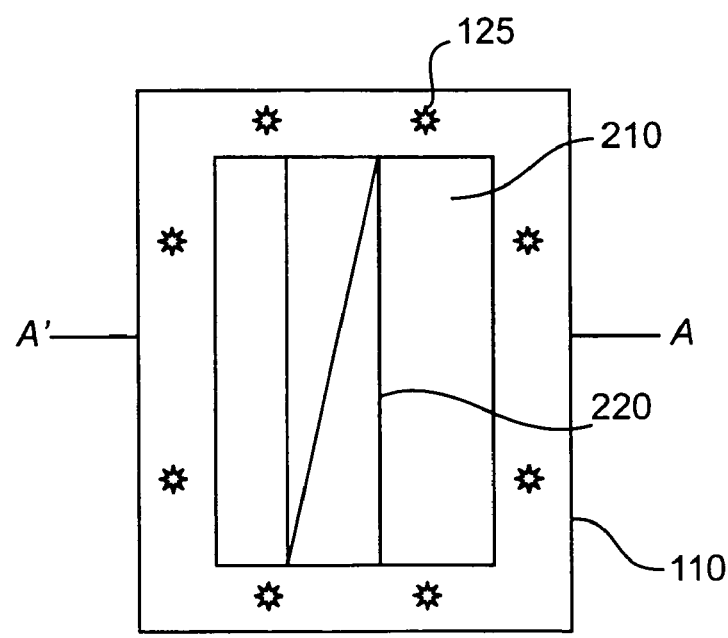

FIG. 2b is a view as shown from line A'–A of the perspective drawing of FIG. 2a. The wires of "Z" pattern 220, submerged in imaging medium 210, are mounted in accurately known locations on the inner wall of jig 110. Tracking markers 125 are shown in this embodiment as surrounding the upper surface of jig 110.

Figure 3A:
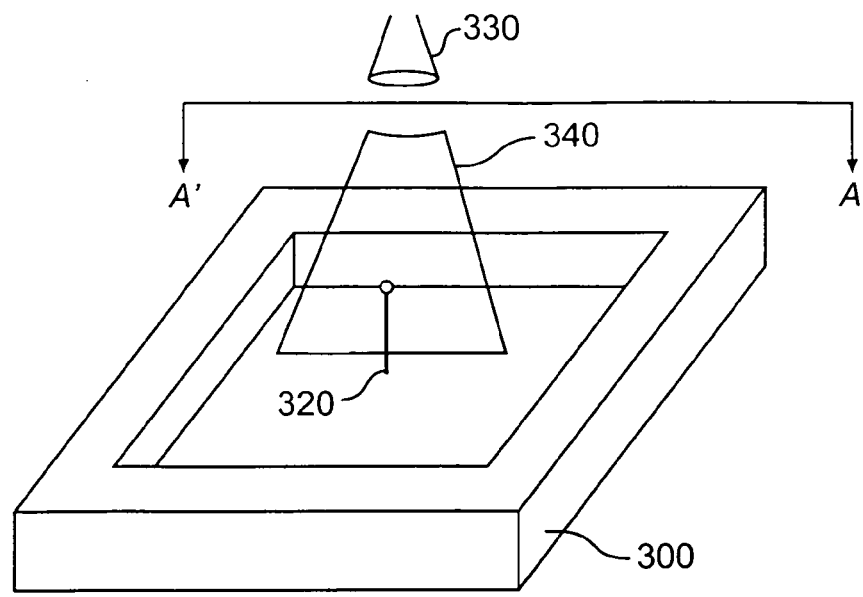
FIG. 3a is a perspective view of an ultrasound probe imaging a jig containing a point target.
Figure 3B:
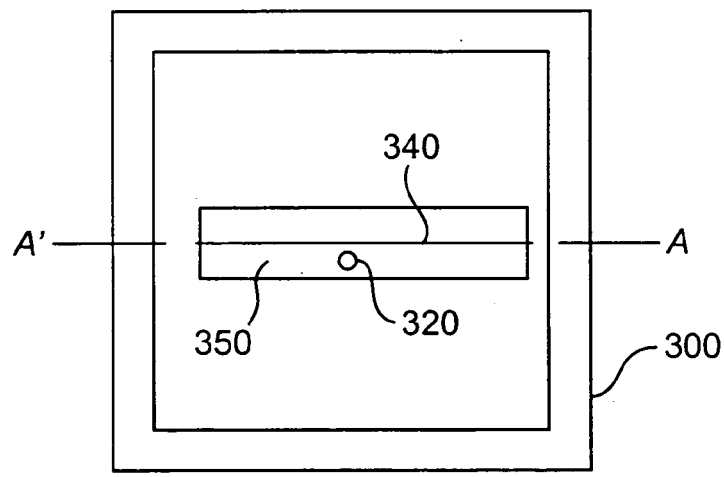
FIG. 3b is a top view of the jig shown in FIG. 3a illustrating the elevation imaging problem due to a non-ideal imaging plane.
Figure 4:
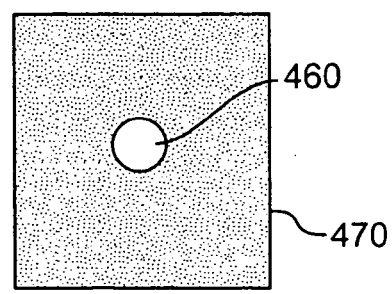
FIG. 4 represents an image of the calibration jig in FIGS. 2a,b formed by an ultrasonic imaging system.

Performing accurate image-based calibration using small point-target like structures, such as a needle tip, can be difficult due to elevation imaging effects. FIG. 3a depicts such a situation where an ultrasound probe 330 is imaging a point target 320. Ideally, no image would be collected from point target 320 until true imaging plane 340 intersects it. The true imaging plane has a negligible thickness and is used as the reference plane for the calibration process. In practice, elevation imaging effects can create an image of point target although the true plane of the ultrasound image may be some distance from point target 320. FIG. 3b, taken from the perspective of line A'–A, shows this situation. True imaging plane 340 is located at some distance away from point target 320; however, due to the elevation effect, point 320 lies within collection plane 350. Collection plane 350 is centered around true plane 340 and has some finite thickness. As shown in FIG. 4, the resulting image 470 collected from jig 300 will display a representation 460 of point target 320, even though ideal plane 340 is at a distance greater than a resolution cell away from point target 320. The elevation effect results in some level of uncertainty when attempting a precise operation such as calibration. To compensate for this uncertainty, a realistic model ultrasound imaging preferably considers the image plane having a non-negligible thickness. Calibration pattern 220 compensates for the elevation imaging problem by providing a line target to produce points which can be used to calibrate the probe.

Figure 5:
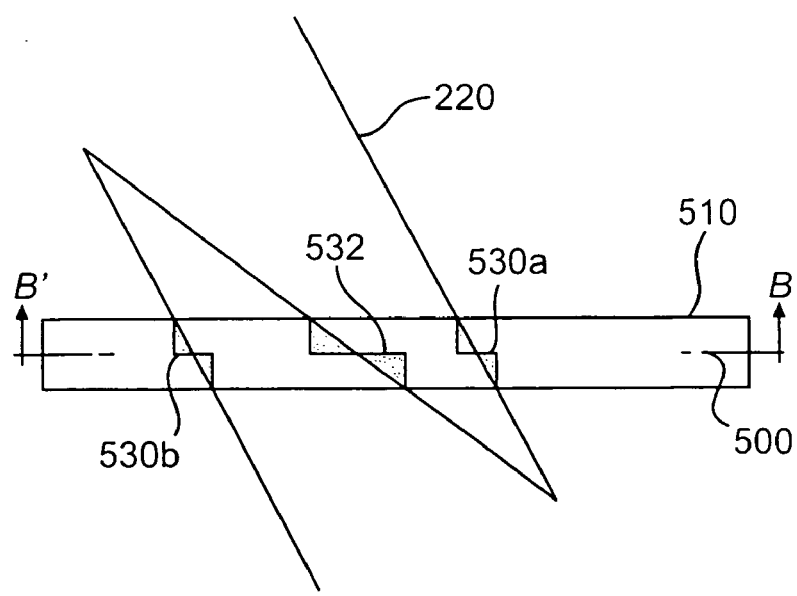
FIG. 5 is a top view showing how the imaging plane intersects an embodiment of a calibration pattern.

FIG. 5 shows a top view of "Z" pattern 220 being intersected by both the true imaging plane 500 and the collection plane 510 of the imaging system. True imaging plane 500, represented in FIG. 5 as line B'–B, has a negligible thickness. Objects captured within this plane will have no elevation errors associated with their location in the image. Collection plane 510, however, has a finite thickness and objects captured within this plane can appear as if they were imaged at the true imaging plane 500, thus creating a position error for these objects in the output image. The "Z" jig compensates for these errors by providing a line target for the calibration points. The line targets of the "Z" pattern 220 pass through the entire thickness of collection plane 510. The resulting image will show an integration of the energy reflected by the wire as it passed through the entire elevation dimension of the collection plane. Shaded portions 530a–b and 532, which can be interpreted as projections of the wire onto the true imaging plane 500, represent the image of the wire in the output image.

Figure 6:
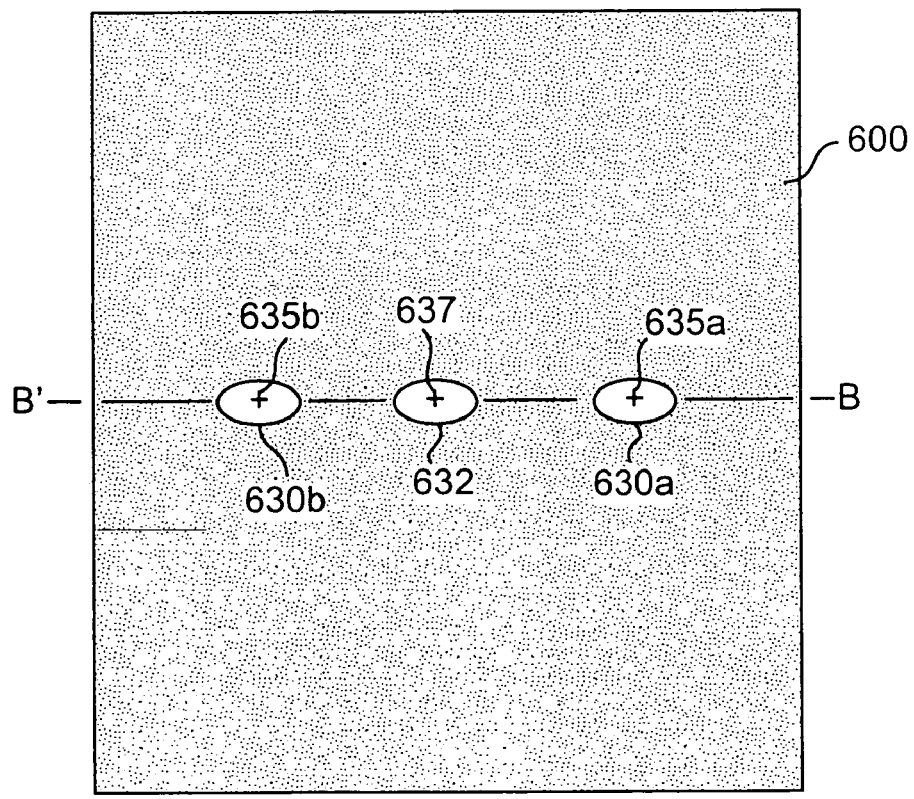
FIG. 6 illustrates an image of the calibration pattern of FIG. 5 showing the intersection points in the image.

FIG. 6 depicts an example of an output image 600 collected from the "Z" pattern 220. The image is taken from the viewing perspective B'–B shown in FIG. 5. Each oval 630a–b and 632 in image 600 represents an intersection of the wire, 530a–b and 532, respectively, with the entire width of collection plane 510. For the calibration problem, the points of interest are where the wires actually intersect the true imaging plane 500; these intersections lie at the centers 635a–b and 637 of each of the ovals 630a–b and 632 respectively. The vertical portions of the centers are interpreted as the centers of the wires 220 in the vertical dimension of image 600. The centers may either be selected manually by the user or automatically by the computer. One advantage of utilizing the "Z" pattern is that in producing centers 635a–b and 637 in image 600, the intersection of the wire with true imaging plane 500 is accurately determined and therefore errors due to the elevation effect are avoided. In order to properly perform the calibration, the coordinates of identical points are preferably found in image space and in probe space. The image point which is used to perform the calibration is center 637 of middle oval 632. These positions, taken over many different images, form a set points defined as calibration points.

Figure 7:
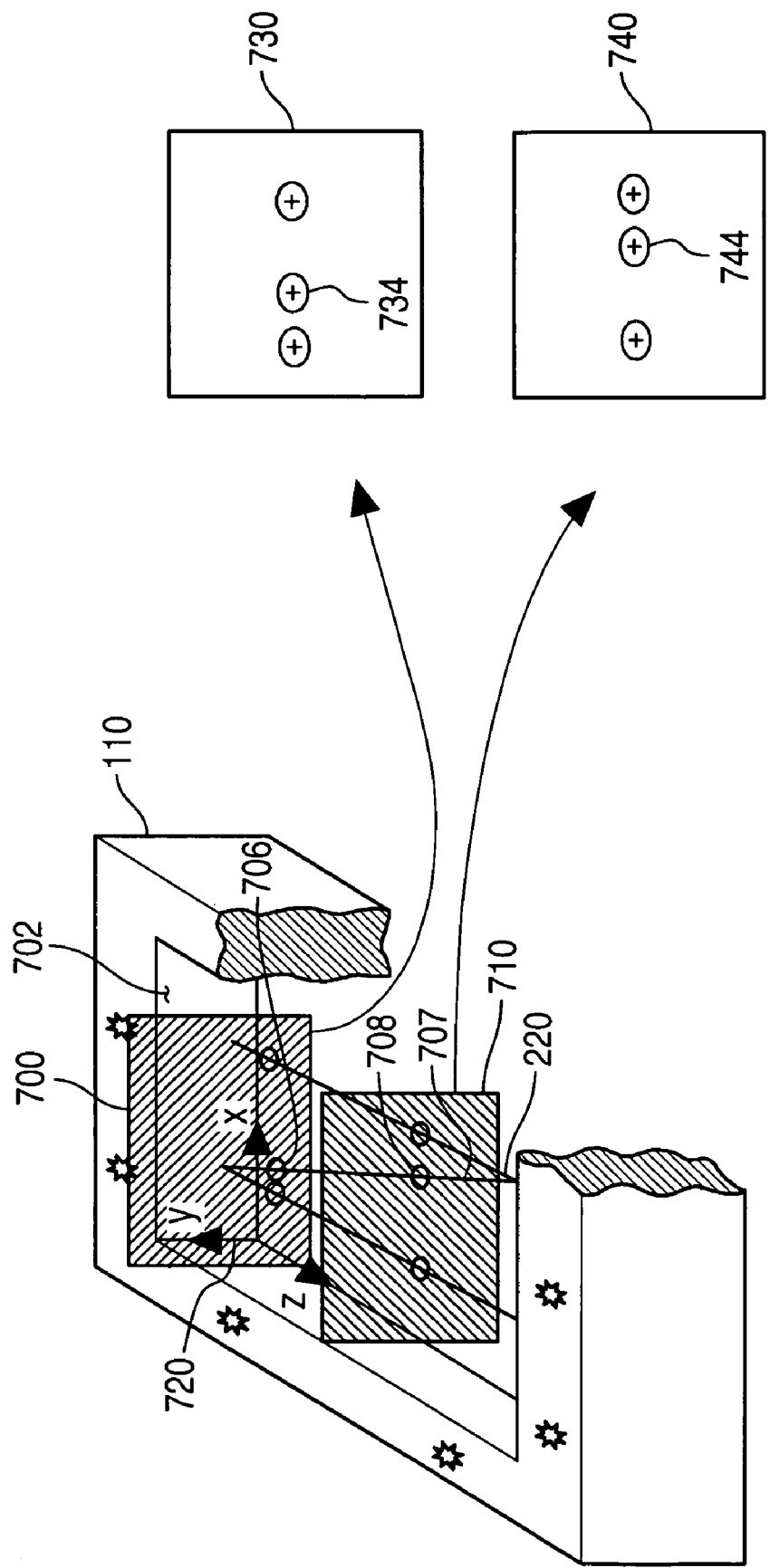
FIG. 7 is a perspective view of an embodiment of a calibration jig showing different planes intersecting a pattern at differing geometries, and the resulting images corresponding to each geometry.

FIG. 7 illustrates the technique of determining the three-dimensional coordinates of calibration points in the calibration jig coordinate system, or jig space, based upon the two outside centers and the middle center. Coordinate system 720 is the reference used to localize points in jig space. The X-Y plane of the coordinate system is the inside wall 702 of jig 110 and the Z-axis lies along the lower inside edge, as shown. First image 730 is the result of placing true imaging plane 700 close to the origin of coordinate system 720. Due to the geometry of the Z pattern, imaging plane 700 intersects diagonal wire 707 of the Z pattern closer to the left wire at point 706. As a result, the center 734 lies closer to the left side of image 730. Second image 740 is the result of placing true imaging plane 710 further from the origin of coordinate system 720. In this instance, imaging plane 710 intersects the diagonal wire 707 of the "Z" pattern closer to the right wire at point 708. The resulting image 740 shows the middle center 744 lying closer to the right side of image. These two examples shown in FIG. 7 illustrate that the lateral position of the middle center in the output image can be directly correlated to the Z coordinate in jig space of the diagonal wire 707 when it intersects the true imaging plane. The X and Y coordinates of the calibration point in jig space are identical to location of the two parallel wires, which are precisely known and remain constant for any value of Z. The technique of determining the Z coordinate is preferably based on the Brown-Roberts-Wells (BRW) method used in some Computer Tomography applications Essentially it computes the ratio of the distances from one of the outside points to the center point and the remaining outside point in order to compute the location in jig space of the calibration point. This technique is well known in the art and is described in the paper "Coordinate Transformation and Calculation of the Angular Depth Parameters for a Stereotactic System," Medical Physics, Vol. 14, No. 6, November/December 1987 by Chen B. Saw, et al., which is incorporated by reference.

Another preferable advantage of employing "Z" pattern 220 over other calibration techniques is the elimination of one axis of movement necessary to position images for calibration. Motion of the imager along the long axis of the "Z" results in the middle center moving laterally in the output image. Thus an automated calibration system would preferably only need to move the imager along the long axis and perpendicular to the axis of a "Z" pattern. Since the calibration point is computed based on the image, preferably, there are no predefined positions for placing the imaging plane within the calibration jig.

Figure 8:
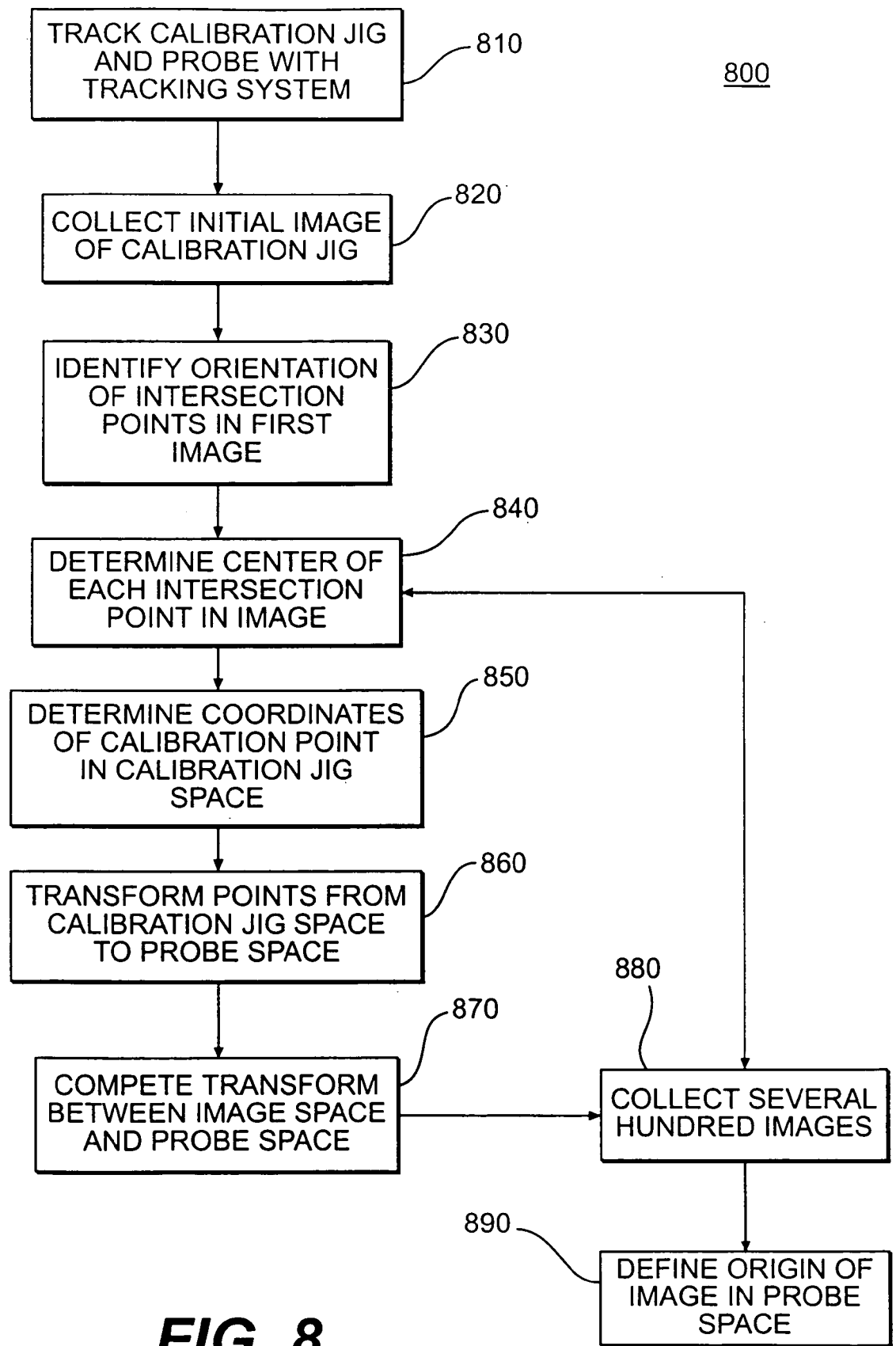
FIG. 8 is a flow chart illustrating methods and systems in accordance with the present invention.

Referring to FIG. 8, the processes or steps associated with calibration procedure is illustrated at 800. Initially, calibration jig 110 and probe 130 are tracked using the surgical tracking system throughout the entire calibration procedure in step 810. An initial image of calibration jig 110 is collected (step 820). From this initial image, the orientation of the intersection points is determined. This could be a automated process carried out by computer 150. However, it is also possible for the user to determine this orientation and provide this information into the computer manually via a keyboard or through a graphical user interface (step 830). In step 840, the center points of each intersection in the initial image is determined, and their pixel location is recorded as its image space coordinate. Again, this step may be performed manually by the user or could be carried out automatically by computer 150. In step 850, the Z coordinate of the calibration point is computed in jig space by determining the ratio of the distance between centers of the two outside intersection points and the distance between the center of one outside intersection point and the center of the middle intersection point. From analysis of these ratios, the position of the calibration (center) point in jig space can be calculated. In step 860, the calibration point is transformed from jig space to probe space. This transformation is readily calculated by computer 150 since both jig 110 and probe 130 positions are known in detector space. Once coordinates of the calibration point are known in both image space and probe space, an initial estimate of the transform relating the two spaces and the scale factor between them is made. Afterwards, points associated with several hundred more images, for example, are calculated and steps 840–870 are repeated on a large set of calibration points to refine the transform and scale factor which relate image space to probe space (step 880). After the transform and scale factors are accurately known, the origin of the image in probe space coordinates is defined which completes the calibration procedure (step 890).

Figure 9:
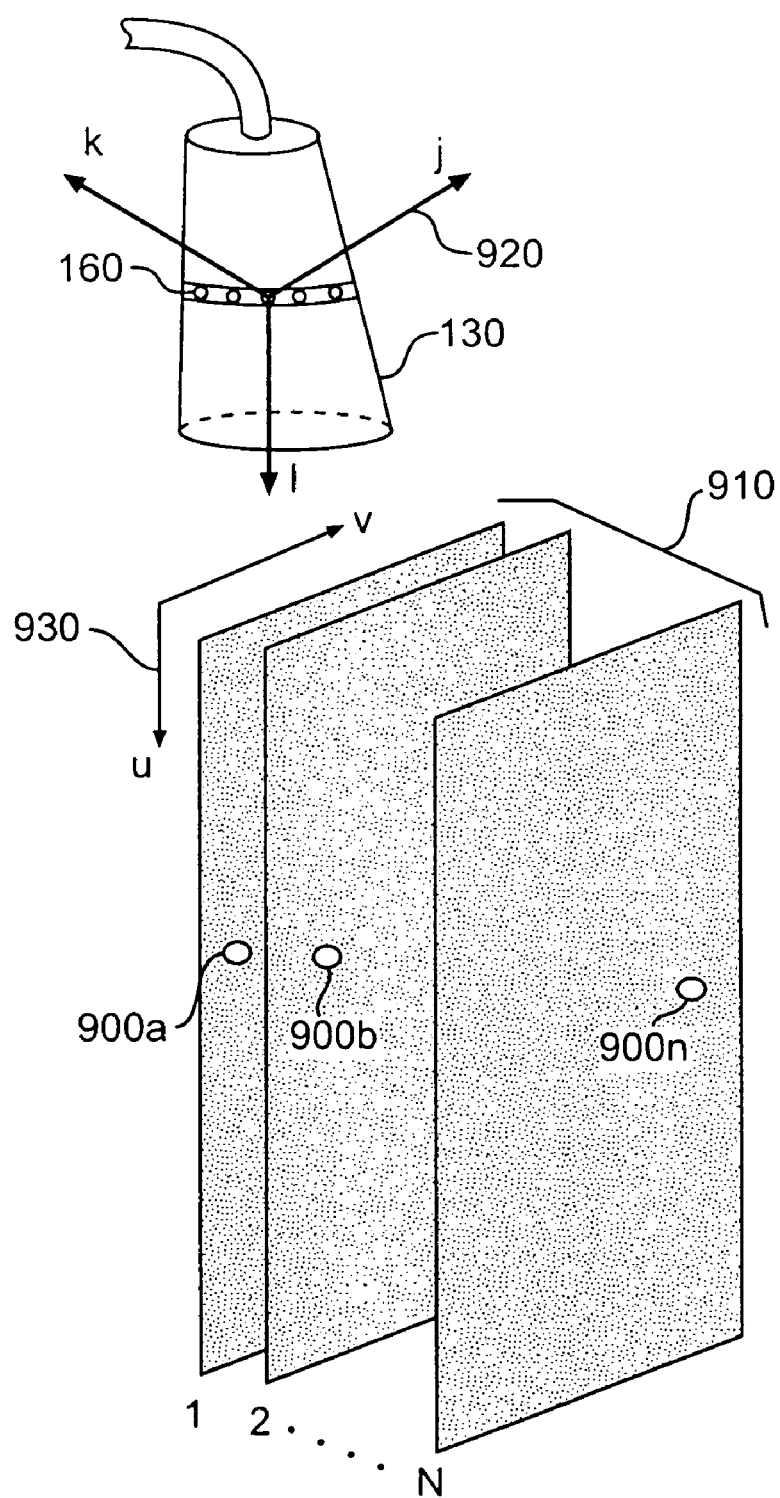
FIG. 9 shows a set of collected images each containing calibration points lying in a different part of the image plane and their relationship to probe space reference.

The goal of the calibration process is to be able to relate points described by pixel locations in image space to positions described in three-dimensional probe space. In order to accomplish this, a mathematical transform between the two spaces, or coordinate systems, is preferably determined. FIG. 9 depicts an exemplary three-dimensional coordinate system, 920, which is referenced to probe 130 and used to describe points in probe space. Coordinate system 930 is a two dimensional coordinate system which is used to describe the location of points within the images. During the calibration process, a set of images 910 is collected. Each image within the set represents calibration pattern 220 as sensed by probe 130 as the probe is moved along the calibration jig's longitudinal dimension (Z axis of coordinate system 720 shown in FIG. 7). The number of images, N, within the set can vary, but typically several hundred are used to perform the calibration. Each of the images within set 910 contains at least one calibration point; however, for purposes of clarity, only one calibration point per image is shown in FIG. 9. As described earlier, the centers of calibration points 900a–n are identified in each image, resulting in at least several hundred image points whose locations in jig space can be calculated. Once this is accomplished, calibration points 900a–n can readily be transformed to probe space referenced by coordinate system 920. The final stage in the calibration process is to utilize the points 900a–n described in both image space and probe space to derive a coordinate transform and scale factor between the two spaces. The computation of this transform is described in detail below.

Figure 10:
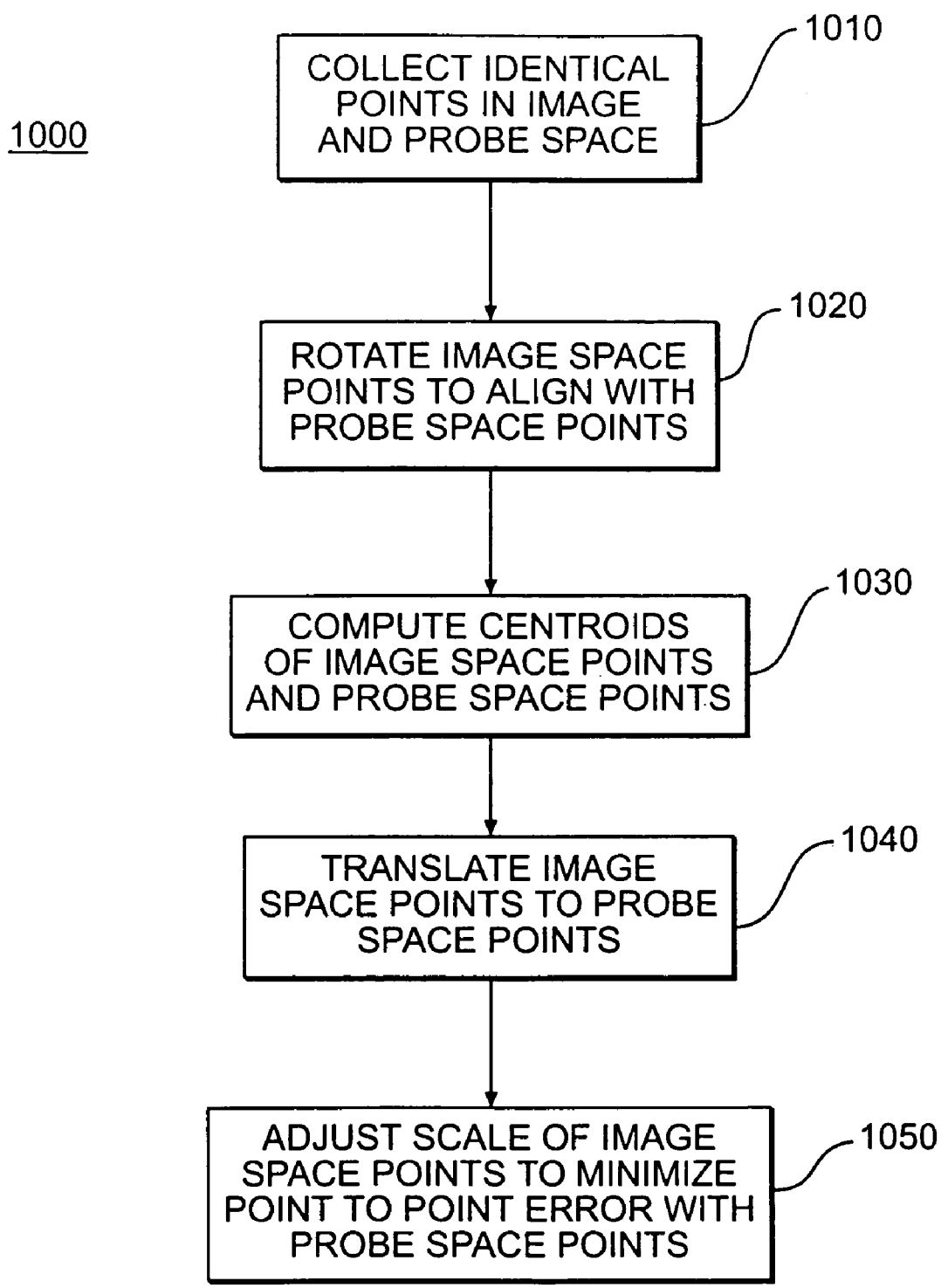
FIG. 10 is a flow chart illustrating the steps of determining a relationship between a probe using two dimensional images.

A technique to derive a transform between two coordinate systems given a set of identical points described in each system is provided in "Closed-form Solution of Absolute Orientation using Unit Quaternions," Journal of the Optical Society of America, Vol. 4, No. 4, April 1987 by Horn, which is incorporated by reference. FIG. 10 presents a brief description of this method 1000 as it applies to the present invention. Initially, identical points described in both image space and probe space are collected in step 1010. Image space points are then rotated so that they align with points given in probe space (step 1020). After rotation, the centroids of all the points in both probe and image spaces are computed. These values are then used to find the translation between the two systems (step 1030). The image space points are then translated in order to align with probe space points (step 1040). Finally, in step 1050, the scale of the image space points is adjusted to minimize the point-to-point error with the probe space points.

Figure 11:
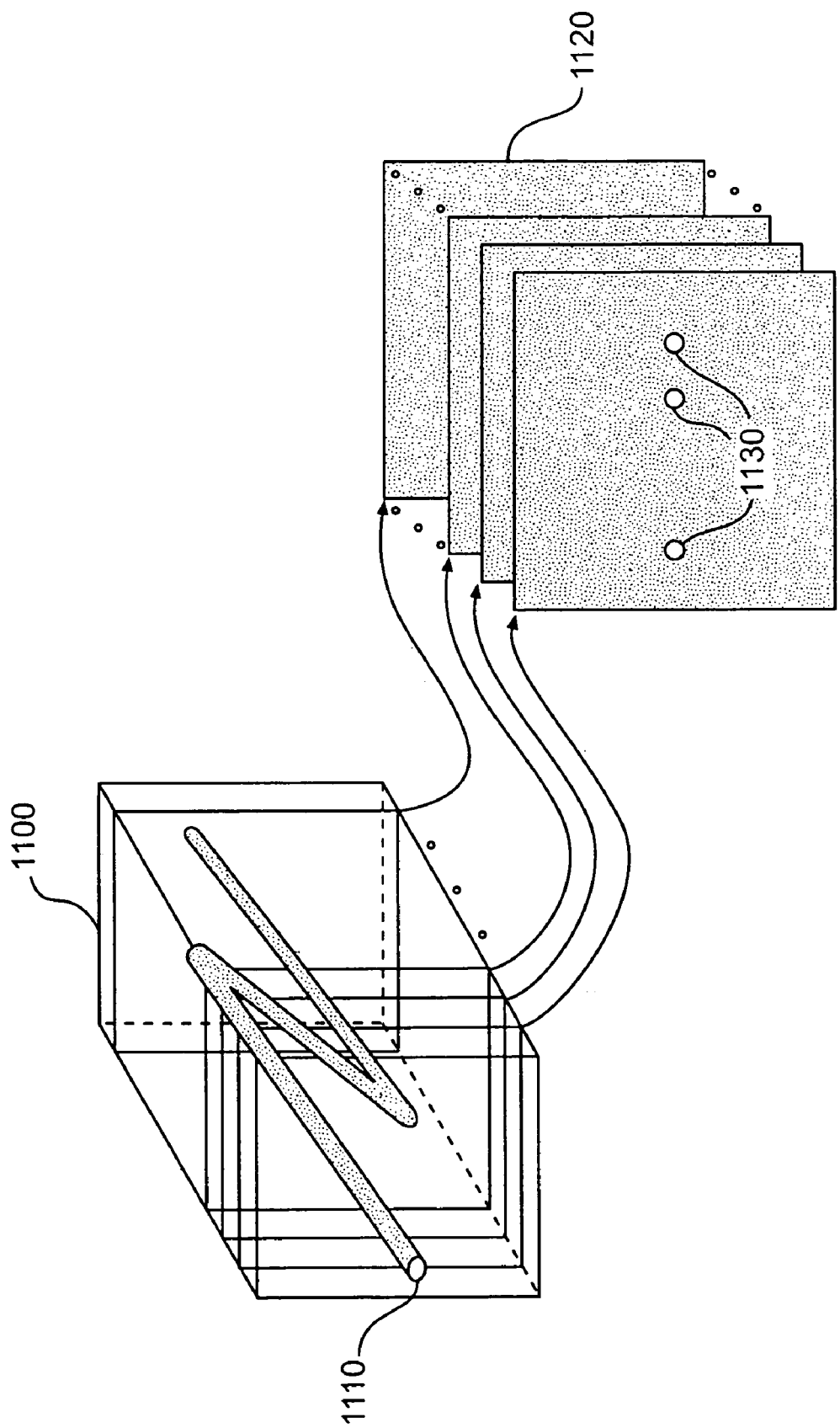
FIG. 11 illustrates an exemplary three-dimensional image of an embodiment of a calibration pattern and its corresponding two dimensional slices of the volumetric image.

Referring to FIG. 11, another embodiment of the invention allows the calibration of image volumes produced by three-dimensional imaging machines, as well as reconstructed volumes from two-dimensional imaging machines. Instead of an image by image collection of intersection points for the calibration, the entire volume is processed 1100. By collecting slices of voxels, or volume element which is the 3-D counterpart to "pixels" associated with the "Z" pattern 1120, the corresponding intersection points 1130 can be computed. Then, by applying the same techniques as previously disclosed herein for the two dimensional calibration, a calibration transform for the volume is computed. The preferred embodiment for a three-dimensional sensor is an ultrasound device; however, other methods of producing three dimensional imagery could also be used within the scope of the present invention.

Figure 12:
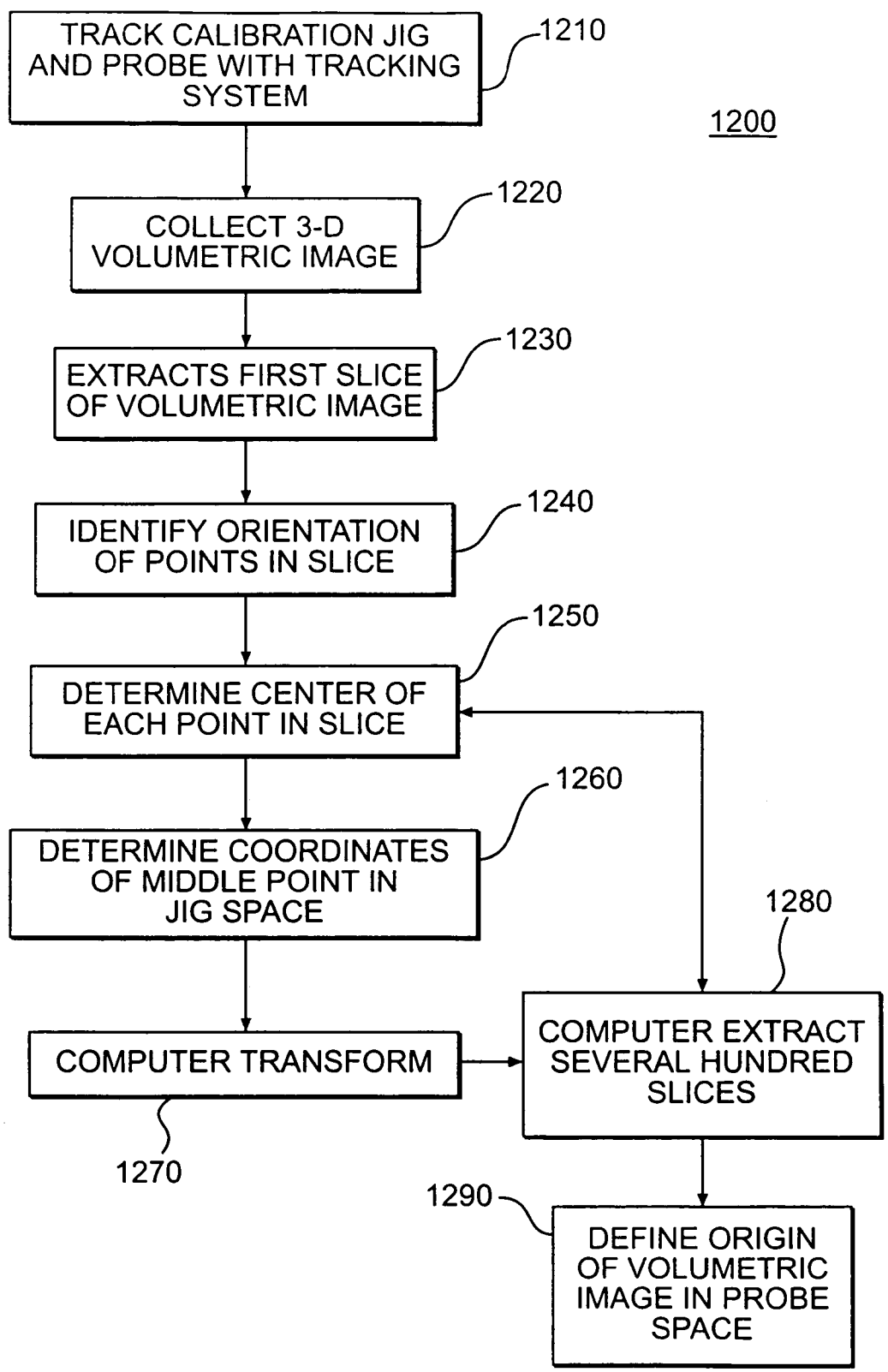
FIG. 12 is a flow chart illustrating methods consistent with the steps of calibrating a probe using a three dimensional image.

Referring to FIG. 12, steps consistent with the present invention for calibrating three-dimensional images are shown (1200). Initially, the calibration jig 110 and probe 130 are tracked with a surgical navigation system (step 1210). A three-dimensional volumetric image is collected and processed with an imaging system (step 1220). A first slice is extracted from the volumetric image and the orientation of the points (1130) in the slice is determined (steps 1230 and 1240). Steps 1230 and 1240 may be performed by the operator. However, they may also be performed automatically by the computer. In step 1250, the centers of the intersections of the "Z" pattern are determined for the first slice. Afterwards, the coordinates for the middle intersection point, or the calibration point, is determined in jig space using the BRW method described earlier (step 1260). In step 1270, an initial transform is computed which relates probe space and image space. Unlike the two-dimensional case, the scale factor is not computed since these factors are already known. After an initial estimate for the transform is made, the computer will extract several hundred more slices (step 1280), for example, and repeat steps 1250–1270 in order to refine the initial estimate of the transform. After the transform is determined, the origin of the volumetric image is described in probe space, completing the calibration procedure (step 1290).

Figure 13:
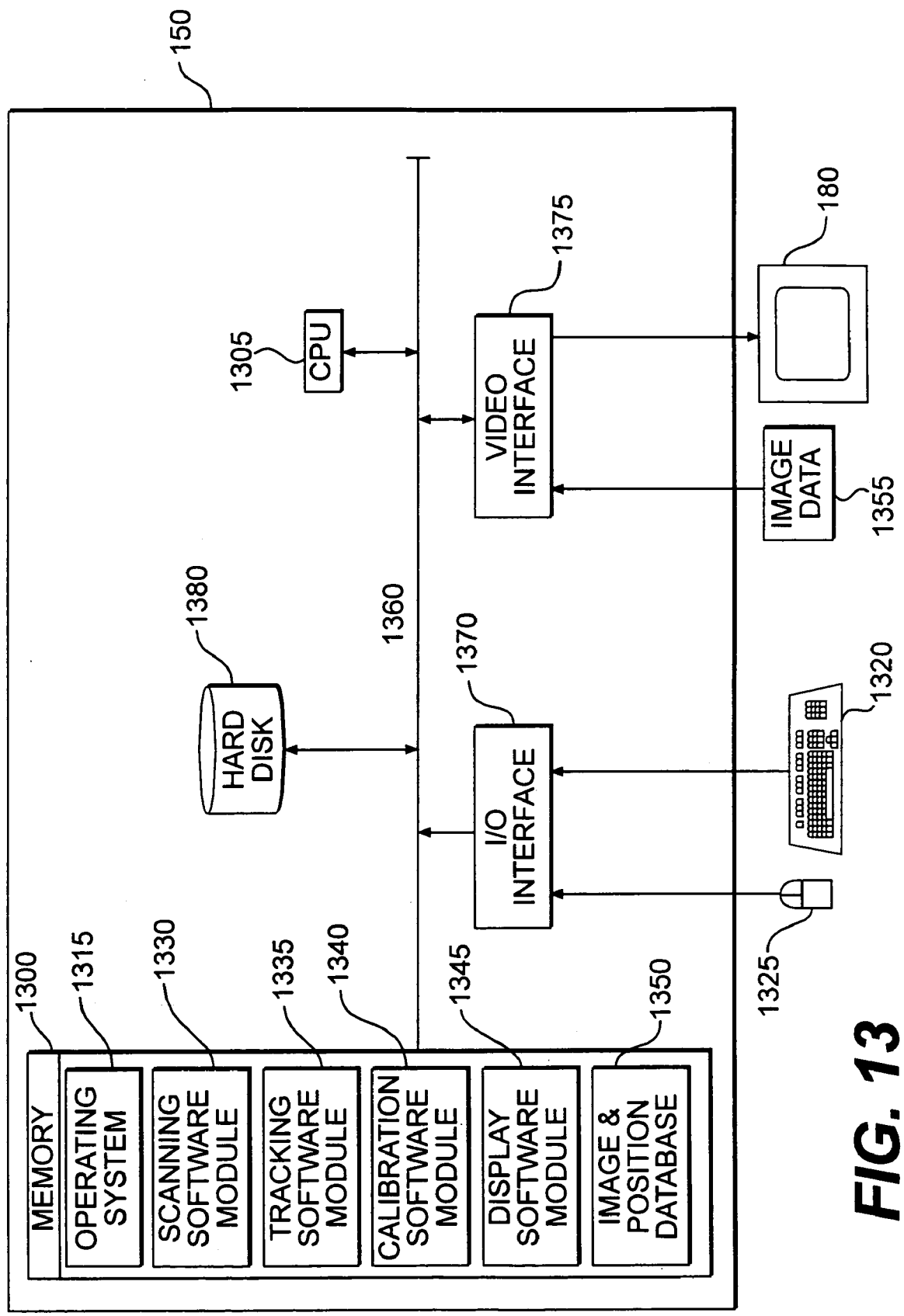
FIG. 13 is a block diagram of an exemplary computer system consistent for use with the present invention.

Referring to FIG. 13, components and modules of a computer system 150 used to perform various processes of the present invention are described. Although a STEALTH STATION® image guided system manufactured by Medtronic Sofamor Danek has been identified, it will be appreciated that the present invention may be utilized with other types of computer systems. One aspect of the computer system 150 includes a graphical user interface system operating in conjunction with a display screen of a display monitor 180. The graphical user interface system is preferably implemented in conjunction with operating system 1315 running computer 150 for displaying and managing the display objects of the system. The graphical user interface is implemented as part of the computer system 150 to receive input data and commands from a conventional keyboard 1320 and mouse 1325. For simplicity of the drawings and explanation, many components of a conventional computer system have not been illustrated such as address buffers, memory buffers, and other standard control circuits because these elements are well known in the art and a detailed description thereof is not necessary for understanding the present invention.

A computer program used to implement the various steps of the present invention is generally located in memory unit 1300, and the processes of the present invention are carried out through the use of a central processing unit (CPU) 1305. Those skilled in the art will appreciate that the memory unit 1300 is representative of both read-only memory and random access memory. The memory unit also contains a database 1350 that stores data, for example, image data and tables, including information regarding the probe, and geometric transform parameters, used in conjunction with the present invention. CPU 1305, in combination with the computer software comprising operating system 1315, scanning software module 1330, tracking software module 1335, calibration software module 1340, and display software module 1345, controls the operations and processes of computer system 150. The processes implemented by CPU 1305 may be communicated as electrical signals along bus 1360 to an I/O interface 1370 and a video interface 1375.

Scanning software module 1330 performs the processes associated with creating a coordinate reference system and reference images for use in connection with the present invention and are known to those skilled in the art. Tracking software module 1335 performs the processes for tracking objects in an image guided system as described herein and are known to those skilled in the art. Calibration software module 1340 computes the coordinates of the calibration points in jig space and implements method to determine the transform between image space and probe space.

Display software module 1345 formats the image data for display on monitor 180 and can identify the center positions of the intersection points in displayed images with icons. Typically these icon are represented as cross-hairs. The display software module also works in conjunction with the graphical user interface and allows the user to determine the orientation of the initial image.

Image data 1355 can be fed directly into computer 150 as a video signal through video interface 1375. Alternatively, the data could also be supplied digitally through I/O interface 1370. In addition, items shown as stored in memory can also be stored, at least partially, on hard disk 1380 if memory resources are limited. Furthermore, while not explicitly shown, image data may also be supplied over a network, through a mass storage device such as a hard drive, optical disks, tape drives, or any other type of data transfer and storage devices which are known in the art.

The foregoing description is present for purposes of illustration and explanation. It is not intended to be exhaustive or to limit the invention to the precise form disclosed, and modifications of variations are possible in light of the above teachings or may be acquired from practice of the invention. The principles of the invention and its practical application enable one skilled in the art to utilize the invention in various embodiments and with various modifications as are suited to the particular use contemplated.

What is claimed is:

1. A method of calibrating a tracking device to an image, comprising:
tracking a position of a calibration jig and a position of a probe;
collecting a plurality of images of at least one calibration pattern of the calibration jig with the probe;
locating centers of intersection points in image space associated with each calibration pattern for each of the plurality of images and extracting a calibration point therefrom;
determining the position for at least one calibration point in probe space for each of the plurality of images;
relating the positions of the calibration points in image space and the positions of said calibration points in probe space;
computing an image space reference position in probe space; and
storing the image space reference position.

2. The method of claim 1 further including:
identifying an orientation of the intersection points in a first image of the plurality of images collected;
computing a position component of the calibration point in calibration jig space by comparing the distances from the center of one of the intersection points near each image edge to the centers of two other intersection points for each image; and
transforming the positions of calibration points described in calibration jig space to positions described in probe space.

3. The method of claim 2 wherein the identification of orientation is performed automatically, specified manually, or combinations thereof.

4. The method of claim 2 further including:
receiving positions of identical calibration points described in image space and described in probe space;
rotating the calibration points described in image space to align with the calibration points described in probe space;
computing centroids of the calibration points described in the rotated image space and the calibration points described in the probe space;
translating the calibration points described in the rotated image space to the calibration points described in probe space; and
adjusting the scale of the calibration points described in the rotated and translated image space to minimize the point to point error with the calibration points described in probe space.

5. The method of claim 1 wherein the plurality of images are collected utilizing a probe comprising an ultrasonic transducer generating and receiving ultrasonic signals and further utilizing a processing system which forms two dimensional images from the ultrasonic signals received by the ultrasonic transducer.

6. The method of claim 1, wherein collecting a plurality of images of at least one calibration pattern includes positioning an ultrasound probe relative to the calibration jig to image the calibration jig with the ultrasound probe;

directing ultrasound waves with the ultrasound probe into a jig space of the calibration jig.

7. A method of calibrating a tracking device to a three-dimensional volumetric image, comprising:

tracking a position of a calibration jig and a position of a probe;

collecting a volumetric image of at least one calibration pattern contained in the calibration jig;

extracting two-dimensional slices from the volumetric image;

locating centers of intersection points in slice space associated with each calibration pattern for each of the plurality of slices and extracting a calibration point therefrom;

determining the position for at least one calibration point in probe space for each of the plurality of slices;

relating the positions of the calibration points in slice space and the positions of said calibration points in probe space;

computing a reference position of the volumetric image in probe space; and storing the reference position of the volumetric image.

8. The method of claim 7 further including:

extracting a first slice from the three-dimensional image;

identifying an orientation of the intersection points in the first slice;

computing a position component of the calibration point in calibration jig space by comparing the distances from the center of one of the intersection points near each slice edge to the centers of two other intersection points for each slice; and transforming the positions of calibration points described in calibration jig space to positions described in probe space.

9. The method of claim 7 further including:

receiving positions of identical calibration points described in slice space and described in probe space;

rotating the calibration points described in slice space to align with the calibration points described in probe space;

computing centroids of the calibration points described in the rotated slice space and the calibration points described in the probe space; and translating the calibration points described in the rotated slice space to the calibration points described in probe space.

10. The method of claim 7 wherein the three-dimensional volumetric image is collected utilizing a probe which is an ultrasonic transducer which generates and receives ultrasonic signals and a processing system which forms the three-dimensional image from the ultrasonic signals received by the ultrasonic transducer.

11. A system for registering a tracking device to an image, comprising:

a means for tracking a three-dimensional position of a calibration jig and a position of a probe;

a means for collecting a plurality of images of at least one calibration pattern on the calibration jig with the probe;

a means for providing the plurality of images to the tracking means;

a means for locating centers of intersection points in image space associated with each calibration pattern for each of the plurality of images and extracting a calibration point therefrom;

a means for determining the position for at least one calibration point in probe space for each of the plurality of images;

a means for relating the positions of the calibration points in image space and the positions of said calibration points in probe space;

a means for computing an image space reference position in probe space; and a means for storing the image space reference position.

12. The system of claim 11 further including:

a means for identifying an orientation of the intersection points in a first image of the plurality of images collected;

a means for computing a position component of the calibration point in calibration jig space by comparing the distances from the center of one of the intersection points near each image edge to the centers of two other intersection points for each image; and a means for transforming the positions of calibration points described in calibration jig space to positions described in probe space.

13. The system of claim 12 wherein the identification means is performed automatically, specified manually, or combinations thereof.

14. The system of claim 12 further including:

a means for receiving positions of identical calibration points described in image space and described in probe space;

a means for rotating the calibration points described in image space to align with the calibration points described in probe space;

a means for computing centroids of the calibration points described in the rotated image space and the calibration points described in the probe space;

a means for translating the calibration points described in the rotated image space to the calibration points described in probe space; and a means for adjusting the scale of the calibration points described in the rotated and translated image space to minimize the point to point error with the calibration points described in probe space.

15. The system of claim 11 wherein the means for collecting images further comprises:

an ultrasonic transducer means for generating and receiving ultrasonic signals; and a processing means for forming two dimensional images from the ultrasonic signals received by the transducer means.

16. A system for calibrating a tracking device to a three-dimensional volumetric image, comprising:

a means for tracking a position of a calibration jig and a position of a probe;

a means for collecting a volumetric image of at least one calibration pattern contained in the calibration jig, coupled to the tracking means;

a means for extracting two-dimensional slices from the volumetric image;

a means for locating centers of intersection points in slice space associated with each calibration pattern for each of the plurality of slices and extracting a calibration point therefrom;

a means for determining the position for at least one calibration point in probe space for each of the plurality of slices;

a means for relating the positions of the calibration points in slice space and the positions of said calibration points in probe space;

a means for computing a reference position of the volumetric image in probe space; and a means for storing the reference position of the volumetric image.

17. The system of claim 16 further including:

a means for extracting a first slice from the three-dimensional image;

a means for identifying an orientation of the intersection points in the first slice;

a means for computing a position component of the calibration point in calibration jig space by comparing the distances from the center of one of the intersection points near each slice edge to the centers of two other intersection points for each slice; and a means for transforming the positions of calibration points described in calibration jig space to positions described in probe space.

18. The system of claim 16 further including:

a means for receiving positions of identical calibration points described in slice space and described in probe space;

a means for rotating the calibration points described in slice space to align with the calibration points described in probe space;

a means for computing centroids of the calibration points described in the rotated slice space and the calibration points described in probe space; and a means for translating the calibration points described in the rotated slice space to the calibration points described in probe space.

19. The system of claim 16 wherein the means for collecting images further comprises:

an ultrasonic transducer means for generating and receiving ultrasonic signals; and a processing means for forming three dimensional images from the ultrasonic signals received by the transducer means.

* * * * *